United States Patent [19]

Hyman

[11] Patent Number: 5,602,000
[45] Date of Patent: *Feb. 11, 1997

[54] METHOD FOR ENZYMATIC SYNTHESIS OF OLIGONUCLEOTIDES

[76] Inventor: Edward D. Hyman, 2100 Sawmill Rd., River Ridge, La. 70123

[ * ] Notice: The portion of the term of this patent subsequent to Dec. 23, 2012, has been disclaimed.

[21] Appl. No.: 464,778

[22] Filed: Jun. 23, 1995

Related U.S. Application Data

[63] Continuation-in-part of Ser. No. 161,224, Dec. 2, 1993, Pat. No. 5,516,664, Ser. No. 100,671, Jul. 30, 1993, and Ser. No. 995,791, Dec. 23, 1992, Pat. No. 5,436,143.

[51] Int. Cl.$^6$ ............... C12P 19/34; C12Q 1/68; C12Q 1/70; A61K 38/43
[52] U.S. Cl. .................. 435/91.1; 435/6; 435/5; 435/91.2; 424/94.1
[58] Field of Search ................ 435/6, 91.1, 5; 424/94.1

[56] References Cited

U.S. PATENT DOCUMENTS

| | | | |
|---|---|---|---|
| 3,850,749 | 11/1974 | Kaufmann et al. | |
| 4,385,112 | 8/1981 | Misaki et al. | 435/6 |
| 4,661,450 | 4/1987 | Kempe et al. | |
| 4,987,071 | 1/1991 | Cech et al. | |
| 5,256,555 | 10/1993 | Milburn et al. | 435/195 |
| 5,273,879 | 12/1993 | Goodman et al. | 435/6 |
| 5,409,817 | 4/1995 | Tabor et al. | 435/74 |
| 5,436,143 | 7/1995 | Hyman | 435/91.2 |

FOREIGN PATENT DOCUMENTS

| | | |
|---|---|---|
| 0196101 | 10/1986 | European Pat. Off. |
| 2169605 | 7/1986 | United Kingdom |

OTHER PUBLICATIONS

Uhlenbeck, The Enzymes vol. XV 31–57, Acad Pres. 1984.
Shum NAR 5: 2297; 1978.
Middleton et al, Analytical Biochem, 144: 110–117, 1985.
Shum et al., "Simplified method for large scale enzymatic synthesis of oligoribonucleotides", Nucleic Acids Res. 5: 2297–2311 (1978).
Schott et al., "Single–step elogation of oligodeoxynulceotides using terminal deoxynucleotidyl transferase", Eur. J. Biochem. 143: 613–620 (1984).
Mackey et al., "New approach to the synthesis of polyribonulceotides of defined sequence", Nature 233: 551–553 (1971).
Hinton et al., "The preparative synthesis of oligodeoxyribonucleotides using RNA ligase", Nucleic Acids Res. 10: 1877–1894 (1982).
England et al., "Dinucleotide pyrophosphates are substrates for T4–induced RNA ligase", Proc. Nat'l Acad Sci. (USA) 74: 4839–4842 (1977).
Beckett et al., "Enzymatic Synthesis of Oligoribonucleotides", in *Oligonucleotide Synthesis: A Practical Approach*, M. J. Gait ed., pp. 185–197 (1984).
Mudrakovskaya et al., "RNA Ligase of Bacteriophage T4. VII: A solid pahse enymatic synthesis of oligoribonucelotides", Biorg. Khim., 17: 819–822 (1991).
Stuart et al., "Synthesis and Properties of Oligodeoxynucleotides with an AP site at a preselected location", Nulceic Acids Res. 15: 7451–7462 (1987).
Norton et al., "A ribonuclease specific for 2'–O–Methyltaed Ribonulceic Acid", J. Biol. Chem. 242: 2029–2034 (1967).
Eckstein et al., "Phosphorothioates in molecular biology", TIBS 14:97–100 (1989).
Bryant et al., "Phosphorothioate Substrates for T4 RNA Ligase", Biochemistry 21: 5877–5885 (1982).
McLaughlin et al., "Donor Activation in the T4 RNA Ligase Reaction", Biochemistry 24: 267–273 (1985).
Ohtsuka et al., "A new method for 3'–labelling of polyribonucelotides by phosphorylation with RNA ligase and its aplication to the 3'–modification for joining reactions", Nulceic Acids Res. 6: 443–454 (1979).
Kornberg, A., "Reversible Enzymatic Sysnthesis of Diphosphopyridine nucleotide and inorganic pyrophosphate", J Biol. Chem. 182: 779–793 (1950).
Kaplan et al., "Enzymatic Deamination of Adenosine Derivatives", J. Biol. Chem. 194: 579–591 (1952).
Bartkiewicz et al., "Nucleotide pyrophosphatase from potato tubers", Eur. J. Biochem. 143: 419–426 (1984).
Rand et al., "Sequence and cloning of bacteriophage T4 gene 63 encoding RNA ligase and tail fibre attachment activities", The EMBO Journal 3: 397–402 (1984).
Heaphy et al., "Effect of Single Amino Acid Chnages in the Region of the Adenylation Site of T4 RNA llgase", Biochemistry 26: 1688–1696 (1987).
Lowe et al., "Molecular cloning and expression of a cDNA encoding the membrane–associated rat intestinal alkaline phosphatase", Biochem. Biophys. Acta 1037: 170–177 (1990).

(List continued on next page.)

*Primary Examiner*—W. Gary Jones
*Assistant Examiner*—Dianne Rees
*Attorney, Agent, or Firm*—Oppedahl & Larson

[57] ABSTRACT

Enzymatic synthesis of oligonucleotides is performed by the steps of: (a) combining a primer and a blocked nucleotide in the presence of a chain extending enzyme to form a primer-blocked nucleotide product containing the blocked nucleotide coupled to the primer at its 3'-end; (b) removing the blocking group from the 3' end of the primer-blocked nucleotide product; and (c) repeating the cycle of steps (a) and (b), using the primer-nucleotide product of step (b) as the primer for step (a) in the next cycle, for sufficient cycles to form the oligonucleotide product. Cycles may optionally include the step of converting any unreacted blocked nucleotide to an unreactive form which is substantially less active as a substrate for the chain extending enzyme. Cycles may also include the step of removing the blocking group from unreacted blocked nucleotide. This step is unnecessary, however, when the same nucleotide is added in two or more successive cycles. The synthetic cycles are preferably performed in a single vessel without intermediate purification of oligonucleotide product.

29 Claims, 10 Drawing Sheets

OTHER PUBLICATIONS

Chang et al., "Molecular Biology of Terminal Transferase", CRC Crit. Rev. Biochem. 21: 27–52.

Razzell et al., "Stduies on Polynucleotides: III. Enzymatic Degaradtion. Substrate Specificity and Properties of Snake Venom Phosphodiesterase", J. Biol. Chem. 234: 2105–2113 (1959).

Tessier et al., "Ligation of Single–Stranded Oligodeoxyribonucleotides by T4 RNA Ligase", Analytical Biochemistry 158: 171–178 (1986).

England et al., "Enzymatic Oligoribonucleotide Synthesis with T4 RNA Ligase", Biochemistry 17: 2069–2076 (1978).

Middleton et al., "Synthesis and Purificationof Oligonucleotides Using T4 RNA Ligase and Reverse–Phase Chromatography", Analytical Biochemistry 144: 110–117 (1985).

Uhlenbeck et al., "T4 RNA Ligase", The Enzymes XV: 31–58 (1982).

Hoffman et al. "Synthesis and reactivity of intermediates formed in the T4 RNA ligase reaction", Nucleic Acids Res. 15: 5289–5301 (1987).

Soltis et al., "Independent Locations of Kinase and 3'–Phosphatase Activities on T4 Polynucleotide Kinase", J. Biol. Chem. 257: 11340–11345 (1982).

Apostol et al., "Deletion Analysis of a Multifunctional Yeast tRNA Ligase Polypeptide", J. Biol. Chem. 266: 7445–7455 (1991).

Becker et al., "The Enzymatic Cleavage of Phospahte Termini from Polynucleotides", J. Biol. Chem. 242: 936–950 (1967).

Greer et al., "RNA Ligase in Bacteria: Formation of a 2',5' Linkage by an *E. coli* Extract", Cell 33: 899–906 (1983).

Schwartz et al., "Enzymatic Mechanism of an RNA Ligase from Wheat Germ", J. Biol. Chem. 258: 8374–8383 (1983).

Beabealashvilli et al., "Nucleoside 5'–triphosphates modified at sugar residues as substrats for calf thymus terminal deoxynucleotidyl transferase and for AMV reverse transcriptase", Biochim. Biophys. Acta 868: 135–144 (1986).

Lehman et al., "The Deoxyribonucleases of *Escherichia coli*", J. Biol. Chem. 239: 2628–2636 (1964).

Singer, M., "Phosphorolysis of Oligonucleotides by Polynucleotide Phosphorylase".

Itakura et al., "Syntethis and Use of Synthetic Oligonucleotides", Ann. Rev. Biochem. 33: 323–356.

Lewin (1987) "Genes: 3rd Ed." pp. 60–63 John Wiley & Sons, N.Y.

Comeron et al, Biochem 16 (23): 5120–5126 (1977).

P. T. Gilham et al, Nature, 233, 551–3, (1971).

UNCONTROLLED METHOD

BLOCKED METHOD

(A) BASIC MODE

(B) PREFERRED MODE

(A) BASIC MODE primer + AppNp

↓ RNA Ligase incubation, then heat inactivate primer-pNp + AMP + AppNp

↓ 3'-Phosphatase incubation, then heat inactivate primer-pN + PO$_4$ + AMP + AppNp Repeat cycle until nucleotide substrate has been added to primer the desired number of times

Fig. 3A

(B) PREFERRED MODE primer + AppNp

↓ RNA Ligase incubation, heat inactivation optional primer-pNp + AMP + AppNp

↓ Exonuclease incubation, then heat inactivate Exonuclease and RNA Ligase primer-pNp + AMP + AppNp ↓ 3'-Phosphatase incubation, then heat inactivate primer-pN + PO$_4$ + AMP + AppNp Repeat cycle until nucleotide substrate has been added to primer the desired number of times

Fig. 3B

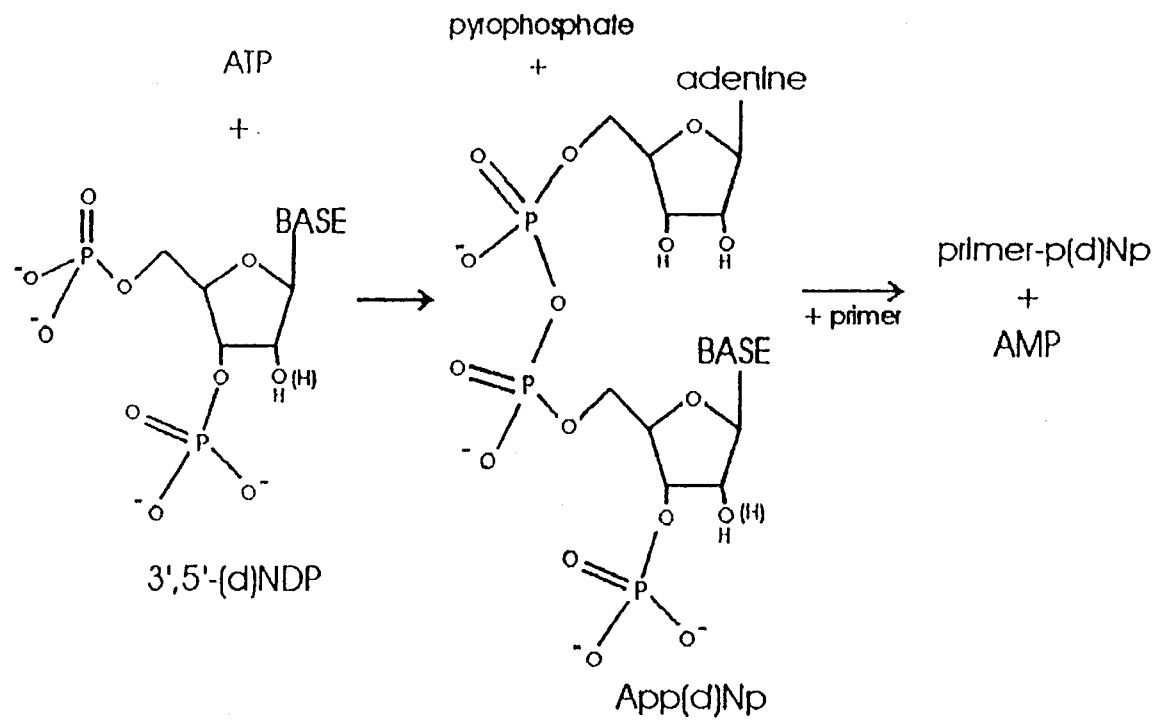
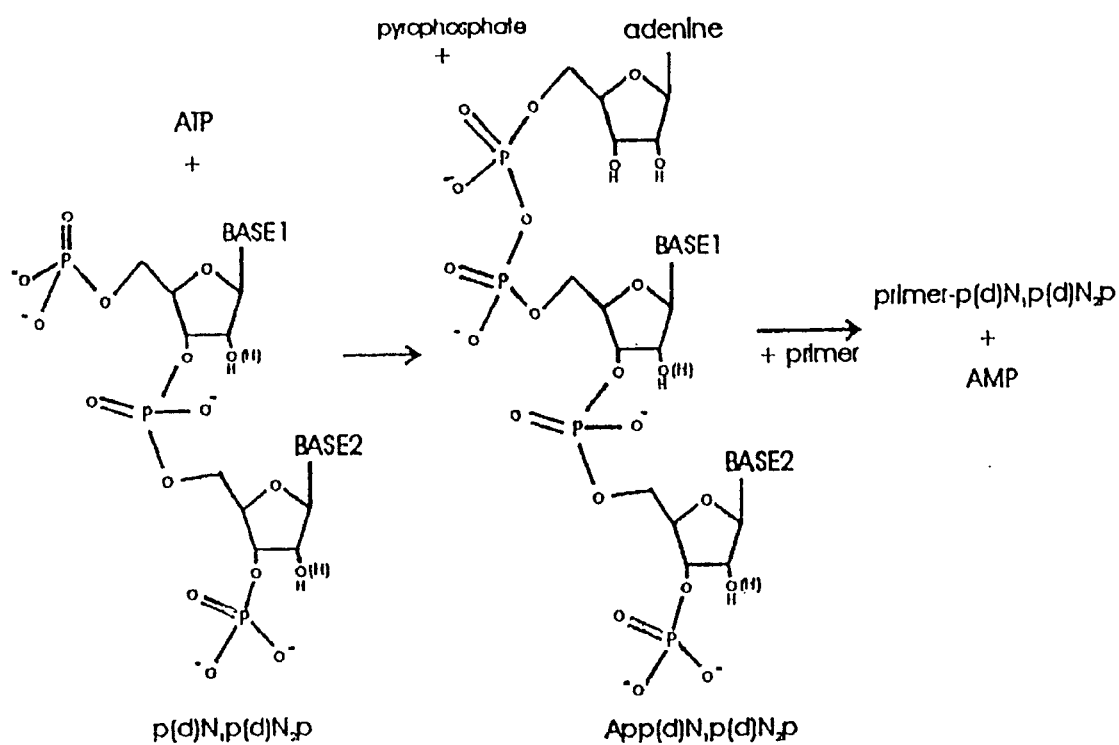
FIGURE 5

METHOD FOR ENZYMATIC SYNTHESIS OF OLIGONUCLEOTIDES

This application is a continuation-in-part of U.S. patent applications Ser. Nos. 08/161,224 filed Dec. 2, 1993, now U.S. Pat. No. 5,516,664 issued May 14, 1996; 08/100,671 filed Jul. 30, 1993 and 07/995,791 filed Dec. 23, 1992 now U.S. Pat. No. 5,436,143 issued Jul. 25, 1995.

BACKGROUND OF THE INVENTION

Synthetic oligonucleotides play a key role in molecular biology research, useful especially for DNA sequencing, DNA amplification, and hybridization. A novel "one pot" enzymatic method is described to replace both the obsolete enzymatic methods and the current phosphoramidite chemical method. This new method promises increased throughput and reliability, ease of automation, and lower cost.

Before the introduction of the phosphoramidite chemical method in 1983, enzymatic methods were used for the synthesis of oligonucleotides. Historically, two distinct enzymatic approaches have been employed as summarized in FIG. 1. These enzymatic methods have been abandoned, however, in favor of the superior phosphoramidite chemical method.

The first enzymatic approach is the "uncontrolled" method. As depicted in FIG. 1A, a short oligonucleotide primer is incubated with the desired nucleotide and a nucleotidyl transferase. At the end of the optimal incubation period, a mixture of oligonucleotide products containing different numbers of bases added to the primer (i.e. primer, primer +1, primer +2 . . . ) is obtained. The desired product, the primer with one added base, is purified using either electrophoresis or chromatography. The process of enzyme incubation and oligonucleotide purification is repeated until the desired oligonucleotide is synthesized. Examples of the use of this approach are: (1) Polynucleotide Phosphorylase ("PNP") and ADP, GDP, CDP, and UDP have been used to make oligodeoxyribonucleotides in accordance with the following reaction:

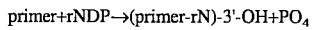

primer+rNDP→(primer-rN)-3'-OH+PO$_4$

Shum et al, *Nucleic Acids Res.*, 5(7): 2297-311 (1978), and (2) Terminal deoxynucleotidyl Transferase and the nucleotides dATP, dGTP, dCTP, and dTTP have been used to make oligodeoxyribonucleotides in accordance with the following reaction:

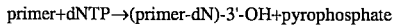

primer+dNTP→(primer-dN)-3'-OH+pyrophosphate

Schott et al, *Eur. J. Biochem*, 143: 613–20 (1984). The flaws of the "uncontrolled" approach are the requirement for cumbersome manual purification of the primer+1 product after each coupling cycle, poor yields of the desired primer+1 product, and inability to automate.

The second enzymatic approach is the "blocked" method, shown in FIG. 1B. The nucleotide used in the extension step is blocked in some manner to prevent the nucleotidyl transferase from adding additional nucleotides to the oligonucleotide primer. After the extension step, the oligonucleotide product is separated from the enzyme and nucleotide, and the blocking group is removed by altering the chemical conditions or by the use of a second enzyme. The oligonucleotide product is now ready for the next extension reaction. Examples of this approach are: (1) PNP and NDP-2'-acetal blocked nucleotides have been used to make oligoribonucleotides. The acetal blocking group is removed under acidic conditions (Gilham et al, *Nature*, 233: 551–3 (1971) and U.S. Pat. No. 3,850,749), (2) RNA ligase and the blocked nucleotide App(d)Np (or ATP+3',5'-(d)NDP) have been used to make oligoribonucleotides and oligodeoxyribonucleotides. The 3'-phosphate blocking group is removed enzymatically with a phosphatase such as alkaline phosphatase (T. E. England et al, *Biochemistry*, (1978), 17(11), 2069–81; D. M. Hinton et al, *Nucleic Acids Research*, (1982), 10(6), 1877–94).

The advantage of the "blocked" method over the "uncontrolled" method is that only one nucleotide can be added to the primer. Unfortunately, the "blocked" method has several flaws which led to its abandonment in favor of the chemical method. The "blocked method", like the "uncontrolled" method, requires the purification of the oligonucleotide product from the reaction components after each coupling cycle.

In the first approach, using PNP, the oligonucleotide is exposed to acid to remove the acid-labile acetal blocking group. Oligonucleotide product must be purified and redissolved in fresh buffer in preparation for the next polymerization reaction for two reasons: (1) PNP requires near neutral pH conditions whereas acetal removal requires approximately pH 1; and (2) the product of the polymerization reaction, PO$_4$, must be removed or it will cause phosphorolysis of the oligoribonucleotide catalyzed by PNP.

In the second approach, using RNA ligase, the art teaches that oligonucleotide product needs to be purified after each cycle because the dinucleotide App(d)N, formed by phosphatase treatment of App(d)Np, is still a suitable substrate for RNA ligase and must be completely removed prior to addition of RNA ligase in the next cycle. England et al., *Proc. Natl. Acad. Sci. USA*, 74(11): 4839–42 (1977). Hinton et al. emphasize the importance of purifying oligonucleotide product after each cycle by stating: "This elution profile [a DEAE-sephadex chromatogram of oligodeoxyribonucleotide product] also demonstrates the absence of either significant contaminating products arising from nucleases or of the reaction intermediate, A-5'pp5'-dUp. The absence of such substances is critical if this general methodology is to be useful for synthesis." Hinton et al, *Nucleic Acids Research*, 10(6):1877–94 (1982). The art also teaches that nucleoside and phosphate by-products generated by phosphatase incubation of the RNA Ligase reaction mixture substantially inhibit RNA Ligase activity and must be removed prior to subsequent RNA ligation steps in order to work usefully. Middleton et al., *Anal. Biochem.*, 144:110–117 (1985).

Two modifications have been devised for the "blocked" method to improve the oligonucleotide product yield and to speed required oligonucleotide product purification after each coupling cycle. The first modification was .the use of a branched synthetic approach (*Oligonucleotide Synthesis: a practical approach*, M. J. Gait editor, (1985), pp. 185–97, IRL Press). This approach improved the yield of final oligonucleotide product, but intermediate purification of oligonucleotide after each coupling cycle was still required. The second modification was the covalent attachment of the primer chain to a solid phase support (A. V. Mudrakovskaia et al, *Bioorg. Khim*, (1991), 17(6), 819–22). This allows the oligonucleotide to be purified from all reaction components simply by washing the solid phase support column. However, product yields are still low, and primer chains which do not couple during a cycle are not removed and are carried over to the next coupling cycle. It appears that the poor coupling efficiency results from steric problems encountered by the enzyme in gaining access to the covalently bound primer chain. Unfortunately, it is not possible to combine these two modifications in an automated manner. The current phosphoramidite chemical method for oligonucleotide synthesis also utilizes a solid phase support to facilitate oligonucleotide purification after each coupling reaction.

The present invention provides a method for enzymatic oligonucleotide synthesis which is preferably performed entirely in a single tube, requiring only temperature control and liquid additions, and not requiring intermediate purifications or solid phase supports. This method is well suited for automation on a liquid handling robot apparatus, allowing the simultaneous preparation of a thousand oligonucleotides per day in microtiter plates. This capability dwarfs the best commercially available instrument which can prepare only four oligonucleotides simultaneously with the phosphoramidite method (Applied Biosystems, Inc.).

SUMMARY OF THE INVENTION

This invention provides a method for enzymatic synthesis of oligonucleotides of defined sequence. The method involves the steps of:

(a) combining an oligonucleotide primer and a blocked nucleotide, or a blocked nucleotide precursor that forms a blocked nucleotide in situ in a reaction mixture, in the presence of a chain extending enzyme effective to couple the blocked nucleotide to the 3'-end of the oligonucleotide primer such that a primer-blocked nucleotide product is formed, wherein the blocked nucleotide comprises a nucleotide to be added to form part of the defined sequence and a 3'- blocking group attached to the nucleotide effective to prevent the addition of more than one blocked nucleotide to the primer;

(b) removing the blocking group from the 3'-end of the primer-blocked nucleotide product to form a primer-nucleotide product; and (c) repeating at least one cycle of steps (a) and (b) using the primer-nucleotide product from step (b) as the oligonucleotide primer of step (a) of the next cycle, without prior separation of the primer-nucleotide product from the reaction mixture, using blocked nucleotides appropriate to the defined sequence of the oligonucleotide being synthesized.

When the defined sequence calls for the same nucleotide to be incorporated more than once in succession, unreacted blocked nucleotide may be reused in the subsequent cycle(s). In this case, the blocking group is selectively removed from the primer-blocked nucleotide product substantially without deblocking of the unreacted blocked nucleotide. Otherwise, the method includes the further step of converting any unreacted blocked nucleotide to an unreactive form which is substantially less active as a substrate for the chain extending enzyme than the blocked nucleotide. The method of the invention is preferably performed in a single reaction vessel, without intermediate purification of oligonucleotide product.

In accordance with one embodiment of the invention, a single cycle comprises the steps in sequence:

(a) incubation of an oligonucleotide primer with RNA ligase and App(d)Np or App(d)N$_1$p(d)N$_2$p or precursors thereof, wherein App is an adenosine diphosphate moiety, and Np, N$_1$ and N$_2$ are a 3'-phosphate-blocked nucleoside moiety, to form a primer-pNp product;

(b) incubation with a Phosphatase; and (c) heat inactivation of the Phosphatase.

By careful selection of the conditions of the reaction with the Phosphatase, the selectivity of the enzymatic dephosphorylation reaction can be controlled, such that unreacted blocked nucleotide substrate is either substantially inactivated when it is not to be reused, and substantially left intact when reuse is desired.

In accordance with a preferred embodiment, a single cycle of the method comprises the steps in sequence:

(a) incubation of an oligonucleotide primer with RNA ligase and App(d)Np or App(d)N$_1$p(d)N$_2$p or precursors thereof;

(b) incubation with an exonuclease and a nucleotide pyrophosphatase (e.g. snake venom phosphodiesterase I);

(c) heat inactivation of the Exonuclease and Nucleotide Pyrophosphatase;

(d) incubation with a Phosphatase; and (e) heat inactivation of the Phosphatase.

BRIEF DESCRIPTION OF THE DRAWINGS

FIGS. 3A and B: The method of the invention for the synthesis of repeat regions of an oligonucleotide.

FIG. 5: Reactions catalyzed by RNA ligase.

DETAILED DESCRIPTION OF THE INVENTION

Figure 1A:
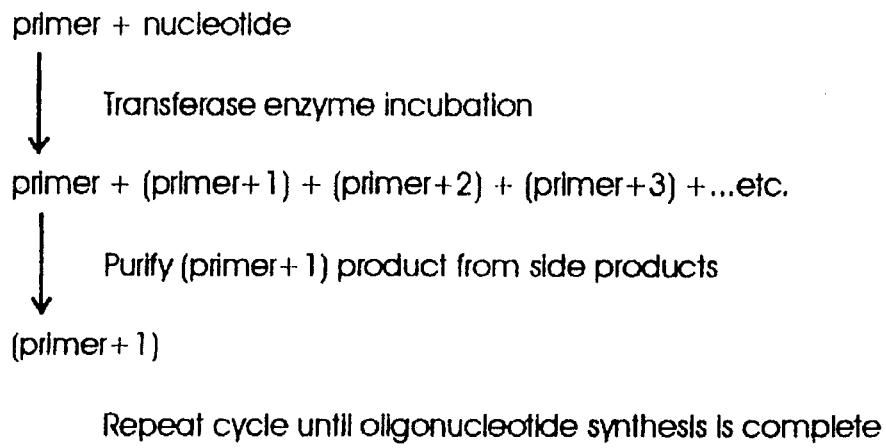
FIGS. 1A and B: The "Uncontrolled" and "Blocked" enzymatic methods previously used for the synthesis of oligonucleotides.
Figure 1B:
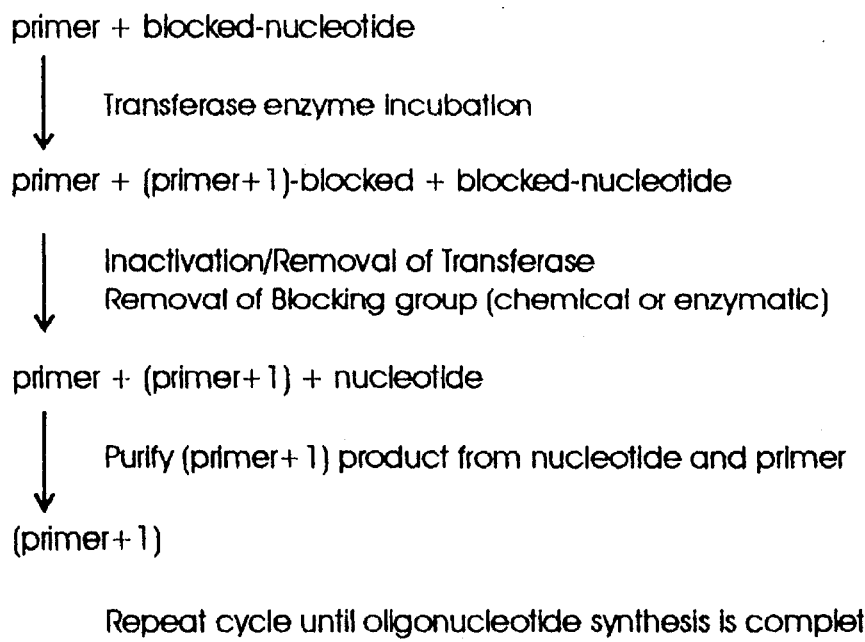
Figure 2A:
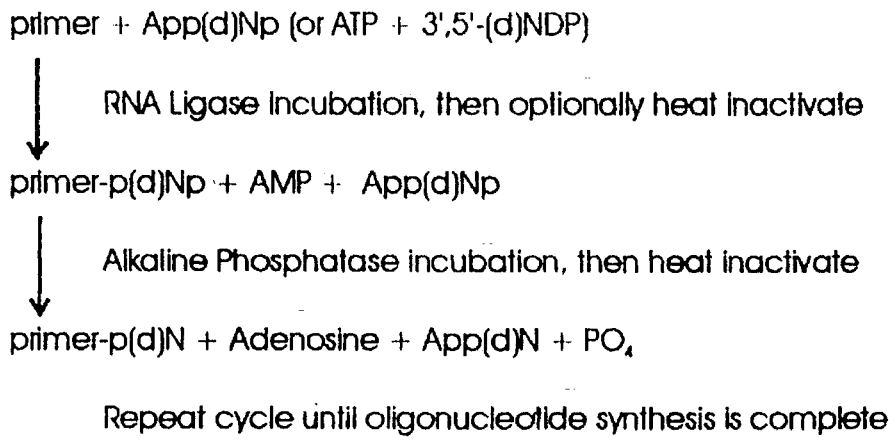
FIGS. 2A and B: The method of the invention for the synthesis of oligonucleotides.

The present invention provides a method for synthesizing oligonucleotides enzymatically which can be performed in a single vessel without the need for any intermediate purification step. An embodiment of the method of the invention in Basic Mode is shown in FIG. 2A. In this embodiment, new nucleotide substrate is added for each new cycle.

As shown in FIG. 2A, a reaction mixture is formed containing an oligonucleotide primer, a blocked nucleotide substrate, and a chain extending enzyme such as RNA ligase and is incubated to couple the blocked nucleotide to the oligonucleotide primer. The RNA ligase may then be inactivated, for example by heating. The resulting reaction mixture contains the primer-blocked nucleotide product, unreacted primer, unreacted blocked nucleotide, and adenosine monophosphate (AMP). Alternatively, the RNA ligase may be left in active form and the substrate rendered inactive for further reaction with the primer.

The next step as shown in FIG. 2A is incubation with an enzyme which removes the blocking group from the primer-blocked nucleotide product and unreacted blocked nucleotide. The resulting reaction mixture, containing unreacted primer, extended primer, and unblocked nucleotide substrate can then be recycled directly for use as the primer in the subsequent cycle without performing intermediate purification of extended primer. Such intermediate purification is taught by prior art as an essential step.

FIG. 3A shows an alternative embodiment of the invention, in which the unreacted blocked nucleotide is recycled to form a region of the oligonucleotide in which the same base is repeated. For example, the 8-mer oligonucleotide 5'-AGUGGCCC-3' contains a consecutive repeat of G and two consecutive repeats of C. Synthesizing the repeat region of this oligonucleotide using the method shown in FIG. 2A results in a significant waste of materials. In this situation it may be preferable when synthesizing the oligonucleotide not to inactivate or deblock the unreacted nucleotide substrate during a cycle, so that the unreacted nucleotide can be reused in the ensuing cycle. This is accomplished by a modification of the method of FIG. 2A which is outlined in FIG. 3A.

As shown in FIG. 3A, the first step is again the addition of a blocked nucleotide to the 3'-end of the primer. In this case, however, the blocking group is selectively removed from the primer-blocked nucleotide product without significantly deblocking, and thus inactivating, the unreacted nucleotide in the reaction mixture using a 3'-phosphatase. The unblocked primer-nucleotide product is then used as the primer for the next cycle and unreacted blocked nucleotide is used as the blocked nucleotide of the next cycle. Similar to the method of FIG. 2A, the modified method for synthesis of repeat regions may be performed without intermediate purification of the extended primer product. This method may be employed for as many cycles as necessary until the repeat region is synthesized.

Figure 4:
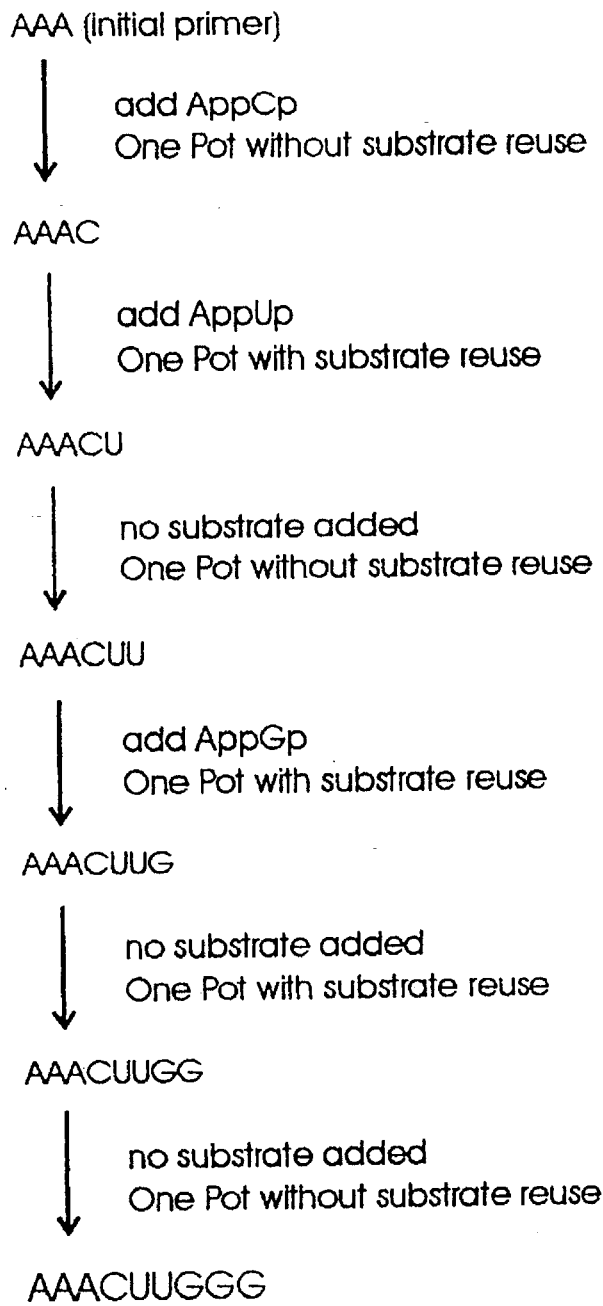
FIG. 4: Synthesis of repeat and non-repeat regions using the method of the invention

In the synthesis of an oligonucleotide with at least one repeat region and at least one non-repeat region, cycles of both methods shown in FIGS. 2A and 3A may be employed to provide an overall synthetic strategy in which repeat regions are synthesized using either method, but preferably the method of FIG. 3A, and non-repeat regions are synthesized using the method of FIG. 2A. A hypothetical synthesis is shown in FIG. 4.

The method of the invention is surprisingly useful because problems identified in the prior art which suggest that the method would not work, have been found by the inventor not to limit the utility of the invention. Prior art (Hinton et al.) teaches that the extended primer product must be separated from the reaction mixture to remove App(d)N, which is able to couple to the primer in the next cycle. It is the discovery of the inventor that the unblocked nucleotide, App(d)N, is substantially less active as a substrate for RNA ligase (e.g. 50 to 100 times less active) than the blocked nucleotide, App(d)Np, obviating the need for separating the unblocked nucleotide from the extended primer product. Prior art (Middleton et al.) also teaches that the nucleoside and phosphate by-product of the phosphatase incubation substantially inhibit RNA ligase, and must be separated from the extended primer product at the end of each cycle in order to work usefully. It is the discovery of the inventor that the by-products of the enzymatic reactions do not significantly inhibit the enzymes, especially RNA ligase.

Experiments were performed by the inventor on each of the reaction by-products confirm the absence of significant inhibition of RNA ligase. The major by-products of the method of the invention are nucleotides and $PO_4$. No inhibition was detected in the presence of 10 mM $PO_4$ and 10 mM Adenosine (a typical nucleoside). Extremely weak inhibition was observed in the presence of 100 mM $PO_4$. In addition, other nucleotides were tested for inhibition: no inhibition was detected in the presence of 10 mM Adenine, 1 mM AMP, 1 mM ATP, 2 mM AppA and 10 mM 3',5'-ADP; extremely weak inhibition was detected in the presence of 10 mM Pyrophosphate; and strong inhibition was observed in the presence of 10 mM AMP and 10 mM ATP. Therefore, the only two products which are strong inhibitors, ATP and AMP, and one product which is an extremely weak inhibitor, pyrophosphate, will never accumulate to these high concentrations since they are degraded by Alkaline Phosphatase.

After the completion of the appropriate number of cycles, the synthesized oligonucleotide may be used in some applications without purification. Alternatively, if purification is required, this can be accomplished using known methods: centrifugation, extraction with organic solvents such as phenol, chloroform and ethyl ether; precipitation, e.g. using ethanol or isopropanol in the presence of high salt concentration; size exclusion, anion exchange, reverse phase, or thin layer chromatography; ultrafiltration or dialysis; gel electrophoresis; hybridization to a complementary oligonucleotide; or by an affinity ligand interaction, such as biotin-avidin. The oligonucleotide may also be attached to a solid support throughout its synthesis, e.g., via the primer, in which case final purification may be performed by washing the support.

The method of the invention may also be used in combination with other methods for synthesizing oligonucleotides such that the method of the invention is used to make a portion of the final oligonucleotide product. Such other methods may include the blocked enzymatic method, the uncontrolled enzymatic method, the branched enzymatic method, chemical methods, transcription-based enzymatic methods, template-based enzymatic methods, and post-synthetic modification methods.

The method of the invention offers numerous advantages by operating in a mild aqueous system. The specificity of the enzymatic reactions obviates the need for base protecting groups, highly reactive functional groups, and harsh solvent conditions. All nucleotide and enzyme reagents are nonhazardous and are stable at room temperature in aqueous solution. In contrast, the phosphoramidite chemical method is encumbered with hazardous solvents, unstable nucleotides, harsh acids and bases, and solid phase supports.

PRIMERS

The primer used in the first cycle of the method of the invention, denoted as the "initial primer" herein, is an oligonucleotide of length sufficient to be extended by the chain extending enzyme. For example, if RNA ligase is the chain extending enzyme, the length is usually at least three-bases. Primers for use in the invention can be made using known chemical methods, including the phosphoramidite method. Other methods include DNase or RNase degradation of synthetic or naturally occurring DNA or RNA. Numerous primers suitable for use in the invention are commercially available from a variety of sources. The initial primer may be selected to provide the first three bases of the ultimate product, or it may be selected to provide facile cleavage of some or all of the initial primer to yield the desired ultimate product.

In most applications, the presence in the oligonucleotide product of the 5'-extension corresponding to the initial primer is inconsequential. These applications may include DNA sequencing, polymerase chain reaction, and hybridization. However, some applications may necessitate the removal of all or part of this 5'-extension. Several procedures have been designed to achieve this result. These procedures are based on a structural or sequence difference between the initial primer and the synthesized oligonucleotide, such that an enzyme can detect the difference and cleave the oligonucleotide into two fragments: an initial primer fragment and the desired synthesized oligonucleotide fragment. Such procedures preferably require only liquid addition to the oligonucleotide solution, and can be categorized by the type of synthesized oligonucleotide for which a procedure can be used: oligodeoxyribonucleotides, oligoribonucleotides, or both types.

OLIGODEOXYRIBONUCLEOTIDES:

(1) Initial primers containing a 3' terminal ribose can be cleaved off with either RNase or alkali. RNase, such as RNase A or RNase One (Promega), hydrolyzes only at the ribose bases of an oligonucleotide.

(2) Initial primers containing a 3' terminal deoxyuridine base can be cleaved off by incubation with Uracil DNA Glycosylase, followed by base catalyzed beta elimination. Stuart et al, *Nucleic Acids Res.*, 15(18): 7451–62 (1987).

OLIGORIBONUCLEOTIDES:

(1) Initial primers containing a 3' terminal deoxyribose base can be cleaved off with DNase. Examples of RNase-free DNases include DNase I and DNase II.

OLIGODEOXYRIBONUCLEOTIDES AND OLIGORIBONUCLEOTIDES:

(1) If the initial primer contains an appropriate recognition sequence then the initial primer can be cleaved off by incubation with an appropriate ribozyme. Alternatively, the initial primer can itself be a ribozyme containing the ribozyme recognition sequence. Cleavage is performed by adjusting reaction conditions or adding a necessary cofactor to turn on the dormant ribozyme activity.

(2) If the initial primer contains an appropriate recognition sequence, then the initial primer can be cleaved off by incubation with an appropriate single-strand-recognizing restriction endonuclease. Examples of such endonuclease include Hha I, HinP I, Mnl I, Hae III, BstN I, Dde I, Hga I, Hinf I, and Taq I (New England Biolabs catalog).

(3) If the initial primer contains a 3'-terminal 2'-O-methyl ribose base, then the initial primer can be cleaved off by incubation with RNase alpha (J. Norton et al, *J. Biol. Chem.*, (1967), 242(9), 2029–34). RNase alpha cuts only at bases containing a 2'-O-methyl ribose sugar.

(4) If the initial primer is composed of some ribose bases, an oligodeoxyribonucleotide specifically annealing to the initial primer and RNase H can be added to cleave off the initial primer.

(5) If the initial primer is composed of some ribose bases, an oligoribonucleotide specifically annealing to the initial primer and a double strand specific RNase such as RNase V1 can be added to cleave the initial primer. If the initial primer is self-annealing, addition of an annealing oligoribonucleotide would not be necessary.

(6) An oligodeoxyribonucleotide may be added which anneals to the initial primer and forms a double stranded DNA region. The initial primer may then be cleaved by addition of an appropriate restriction enzyme. The initial primer can also be a self-annealing oligodeoxyribonucleotide, obviating the need to add an annealing oligodeoxyribonucleotide.

(7) If the initial primer contains a unique ribose base absent from the synthesized oligonucleotide, then the initial primer can be cleaved by incubation with an appropriate base-specific Ribonuclease. Examples include RNase $CL_3$ (cleaves after cytosine only), RNase $T_1$ (cleaves after guanosine only), and RNase $U_2$ (cleaves after adenosine only).

(8) If the synthesized oligonucleotide contains at least one phosphorothioate internucleotidic linkage, and the initial primer does not contain any phosphorothioate internucleotidic linkages, then the initial primer can be cleaved off by incubation with an appropriate nuclease or 5'→3' exonuclease, which is unable to hydrolyze phosphorothioate internucleotidic linkages, or hydrolyzes them poorly.

After cleaving off the initial primer from the synthesized oligonucleotide, the initial primer may be selectively degraded to nucleosides or nucleotides. This technique is based on the differential presence of a terminal phosphate monoester on the initial primer and on the synthesized oligonucleotide and the use of differential digestion with an appropriate exonuclease. Three techniques may be employed.

If the cleavage results in a 5'-phosphate on the synthesized oligonucleotide fragment and a 5'-hydroxyl on the initial primer fragment, then subsequent incubation with spleen phosphodiesterase II (a 5' to 3' exonuclease) will selectively hydrolyze the initial primer fragment to nucleotides. The 5'-phosphate protects the synthesized oligonucleotide from hydrolysis.

If the cleavage results in a 3'-hydroxyl group on the initial primer fragment and a 3'-phosphate on the synthesized oligonucleotide fragment, the initial primer fragment can be degraded using a 3' to 5' exonuclease. This can be accomplished by cleaving off the initial primer prior to the removal of the terminal 3'-phosphate blocking group from the synthesized oligonucleotide. Suitable exonucleases include exonuclease I, phosphodiesterase I and polynucleotide phosphorylase.

If the cleavage results in a 5'-hydroxyl group on the synthesized oligonucleotide fragment and a 5'-phosphate on the initial primer, then the initial primer fragment can be degraded using a 5' to 3' exonuclease with a substantial preference for 5'-phosphate substrates such as lambda exonuclease. This can be accomplished by phosphorylating the oligonucleotide at the 5'-end prior to cleavage, e.g. using polynucleotide kinase.

The cleavage of the oligonucleotide and digestion of the initial primer can be performed at any cycle of the synthesis. For bulk synthesis of a single oligonucleotide, it is preferably performed at the end of the synthesis. For synthesis of multiple oligonucleotides simultaneously, it is preferably performed after synthesizing the first three bases of the oligonucleotide. Further, it will be appreciated that the cleavage does not necessarily need to occur at the junction of the initial primer region and the synthesized oligonucleotide region.

CHAIN EXTENDING ENZYME

The chain extending enzyme used in the method of the invention is preferably RNA ligase. RNA ligase is commercially available from numerous suppliers and has been well characterized in the literature. The reactions catalyzed by RNA ligase relevant to the invention are shown in FIGS. 5A and B.

RNA ligase possesses a number of properties which make it particularly useful in the invention:

(1) The coupling reaction catalyzed by RNA ligase is thermodynamically favorable. In the presence of an AMP inactivating enzyme, the coupling reaction is irreversible.

(2) RNA ligase couples numerous nucleotide analogs, allowing the synthesis of oligonucleotides containing these analogs using the method of the invention. Modifications include base analogs, sugar analogs, and internucleotide linkage analogs. Uhlenbeck et al, *The Enzymes*, vol. xv, pp. 31–58, Academic Press (1982) and Bryant et al, *Biochemistry*, 21:5877–85 (1982).

(3) RNA ligase couples both ribose and deoxyribose nucleotides, allowing the synthesis of oligodeoxyribonucleotides, oligoribonucleotides, and mixed ribose/deoxyribose oligonucleotides using the method of the invention.

(4) RNA ligase nucleotide substrate can be up to two bases in length in the method of the invention; i.e., App(d)N$_1$p(d)N$_2$p or p(d)N$_1$p(d)N$_2$p..

While RNA Ligase is the preferred chain extending enzyme for use in the present invention, other enzymes are within the scope of the invention. For example, because T4 RNA Ligase requires replenishment after each cycle due to its thermal instability, further refinement of the method is anticipated by the use of a thermostable RNA Ligase. A thermostable RNA Ligase is workable since the presence of RNA Ligase in other steps of a cycle is not deleterious. A thermostable RNA Ligase could be added in the first cycle and would not need replenishment throughout the oligonucleotide synthesis, reducing the expense of RNA Ligase per synthesis. Furthermore, a thermostable RNA Ligase with activity at elevated temperatures (65° to 95° C.) may provide the added benefit of reducing primer secondary structure interference with the coupling reaction. Another potential benefit of a thermostable enzyme is high activity at high ionic strength. One probable source of a thermostable RNA Ligase is thermophilic archeabacteria.

Man-made genetic mutants of T4 RNA Ligase useful in the invention without modification include a mutant version with the improved ability to extend an oligodeoxyribonucleotide primer, and a mutant version which is not inactivated at elevated temperatures.

Several other enzymes are denoted in the literature as "RNA Ligases", i.e., Transfer RNA Ligase and HeLa/Eubacterial RNA Ligase. These enzymes differ from T4 RNA Ligase in their substrate requirements in that they are reported in the literature as unable to extend a primer containing a 2'-hydroxyl, 3'-hydroxyl terminus. Consequently, they are not considered as RNA Ligase in this invention Nevertheless, these other enzymes do have the ability to act as chain extending enzymes within the scope of the present invention.

Transfer RNA Ligase is reported in the scientific literature to catalyze a reaction similar to T4 RNA Ligase, but absolutely requiring a primer with a 2'-phosphate and 3'-hydroxyl terminus. Transfer RNA Ligase has been characterized in several eukaryotes, including yeast (Apostol et al, *J. Biol. Chem.*, 266:7445–55 (1991)) and wheat germ (Schwartz et al, *J. Biol. Chem.*, 258: 8374–83 (1983)). Based on the fact that it is essential in transfer RNA processing, Transfer RNA Ligase should be ubiquitous in eukaryotes. Transfer RNA Ligase is a single polypeptide containing three distinct enzyme activities: ligase, cyclic phosphodiesterase, and 5'-polynucleotide kinase. It is the Ligase activity which catalyzes the ligation reaction described above for Transfer RNA Ligase. Since these separate activities have been mapped to separate locations on the polypeptide, it is conceivable that a mutant (e.g. a deletion mutant) can be constructed which contains only the ligase activity.

Figure 6:
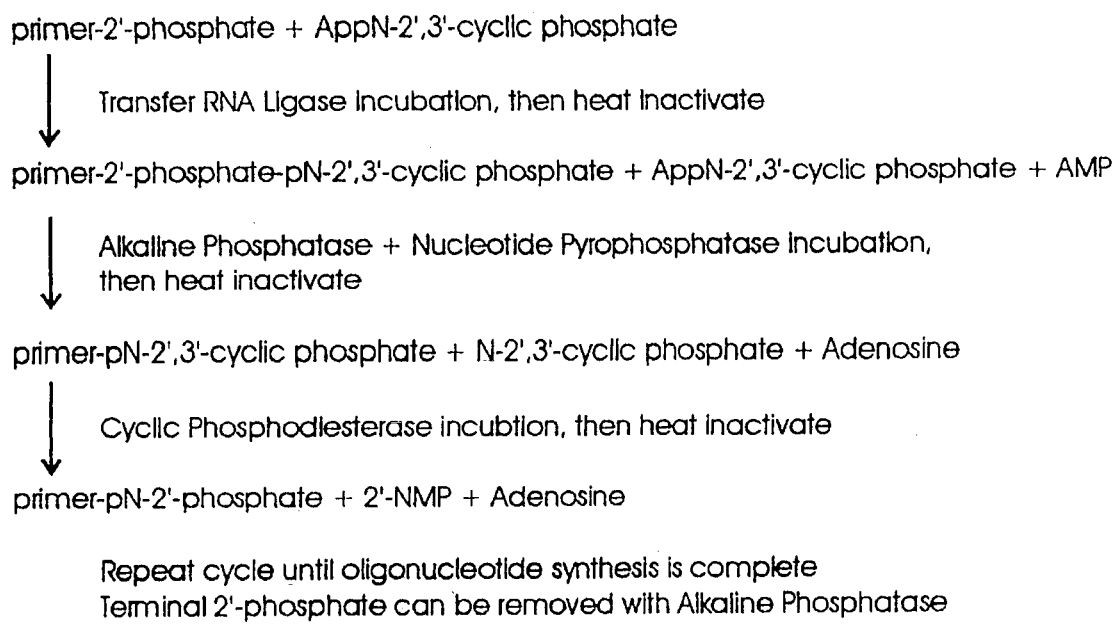
FIG. 6: An embodiment of the invention utilizing Transfer RNA ligase-as the chain extending enzyme.

An embodiment of the method of the invention employing Transfer RNA Ligase or the mutant form as a chain extending enzyme is shown in FIG. 6. Blocked nucleotide substrate, AppN-2',3'-cyclic phosphate, is coupled to a primer-2'-phosphate by the ligase. The second step is inactivation of unreacted blocked nucleotide substrate with Nucleotide Pyrophosphatase, e.g. snake venom phosphodiesterase I, and removal of the 2'-phosphate with a Phosphatase, e.g. Alkaline Phosphatase. (Phosphatase removal of 2'-phosphate may be unnecessary). The Phosphodiesterase I also removes unextended primer chains. The third step is incubation with cyclic phosphodiesterase to remove the blocking group from the 3' end of the extended primer by converting the terminal 2',3'-cyclic phosphate to 2'-phosphate. Such a cyclic phosphodiesterase enzyme is one of the components of Transfer RNA Ligase, whose activity has been isolated by mutation. Apostol et al., *J Biol. Chem.* 266:7445–7455 (1991). The cycle is then repeated until the desired sequence is obtained. Conceivably, the nucleotide substrate reuse technique can also be implemented if Nucleotide Pyrophosphatase is not added and the cyclic phosphodiesterase has the desired substrate selectivity.

Figure 7:
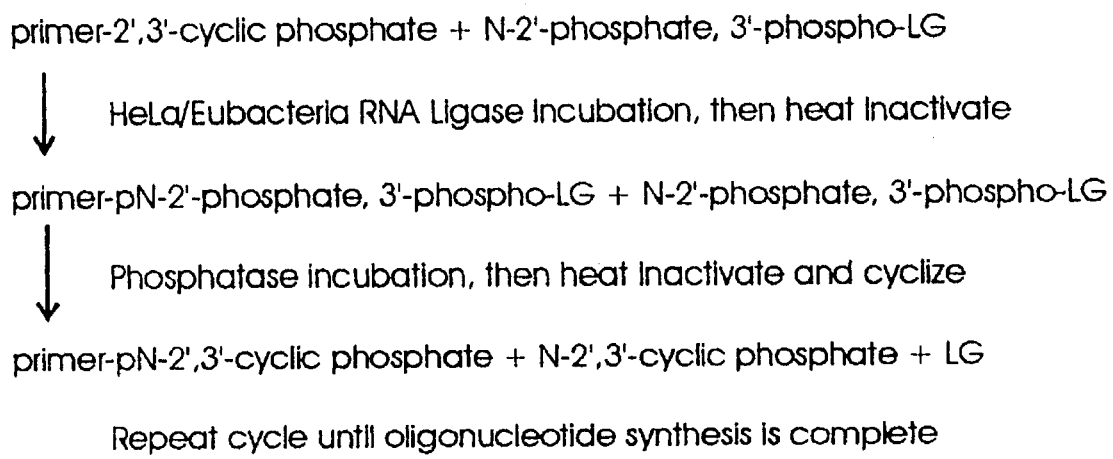
FIG. 7: An embodiment of the invention utilizing HeLa/Eubacterial RNA Ligase as the chain extending enzyme.

HeLa/Eubacterial RNA Ligase catalyzes the reaction: primer-2',3'-cyclic phosphate+5'-hydroxyl-nucleotide substrate →primer-nucleotide, by direct nucleophilic attack of the 5'-hydroxyl of the nucleotide substrate on the cyclic phosphate. The HeLa RNA Ligase forms a normal 3'-5'-phosphodiester linkage; the Eubacterial RNA Ligase forms an unusual 2'-5' phosphodiester linkage (Greer et al, *Cell*, vol. 33, 899–906). An embodiment of the invention employing HeLa or Eubacterial RNA Ligase as the chain extending enzyme is shown in FIG. 7. N-2'-phosphate, 3'-phospho-LG is used as the blocked nucleotide substrate, wherein LG is a good leaving group for nucleophilic displacement (such as dinitro-phenol or 5'-AMP) and the nucleoside N has a free 5'-hydroxyl. The first step is HeLa or Eubacterial RNA Ligase incubation with a primer-2',3'-cyclic phosphate and blocked nucleotide substrate to form primer-blocked nucleotide product. The second step is Phosphatase incubation to remove the 2'-phosphate protecting group. Spontaneously or upon heating, the terminal 3'-phospho-LG will cyclize non-enzymatically to form 2',3'-cyclic phosphate. The cyclized unreacted nucleotide is probably a weaker or inactive substrate for the RNA Ligase in the next cycle.

Terminal deoxynucleotidyl Transferase (TdT) is incapable of coupling its corresponding 3'-phosphate nucleotide substrate analog, dNTP-3'-phosphate. A suggestion has been made in the literature for producing a mutant form of TdT capable of coupling dNTP-3'-phosphate. (Chang et al, *CRC Critical Reviews in Biochemistry*, 21(1): 27–52). Such a mutant form would be a useful chain extending enzyme for the method of the invention.

NUCLEOTIDE SUBSTRATES

The blocked nucleotide substrate employed in the method of the invention is selected for compatibility with the chain extending enzyme, but generally comprises an activated nucleotide and a blocking group. The blocking group is bonded to the nucleotide so as to block reaction of the 3'-hydroxyl group of the nucleotide. Such a nucleotide substrate is referred to generally herein as a "3'-blocked nucleotide."

As used herein, the term "3'-phosphate-blocked nucleotide" refers to nucleotides in which the hydroxyl group at the 3'-position is blocked by the presence of a phosphate containing moiety. Examples of 3'-phosphate-blocked nucleotides in accordance with the invention are nucleotidyl-3'-phosphate monoester/nucleotidyl-2',3'-cyclic phosphate, nucleotidyl-2'-phosphate monoester and nucleotidyl-2' or 3'-alkylphosphate diester, and nucleotidyl-2' or 3'-pyrophosphate. Thiophosphate or other analogs of such compounds can also be used, provided that the substitution does not prevent dephosphorylation by the phosphatase.

When RNA ligase is employed as the chain extending enzyme, the choice of substrate influences the course of the reaction, as can be seen from a consideration of the following reaction mechanism:

(1) E+ATP ←→ E-AMP+pyrophosphate
(2) E-AMP+3',5'-(d)NDP ←→ E[App(d)Np]
(3) E[App(d)Np]+primer-3'-OH ←→ (primer-p (d)N)-3'-phosphate+AMP+E wherein App is an adenosine diphosphate moiety and Np is a 3'-phosphate blocked nucleoside moiety, preferably a 3'-phosphate monoester. The use of precursor nucleotides, ATP+3',5'-(d)NDP, results in a short lag period in the coupling reaction in which the concentration of App(d)Np must build up to sufficient levels in solution before step 3 can occur. The use of pre-activated nucleotide substrate, App(d)Np, avoids a lag period, allowing step 3 to occur instantly. Therefore, faster and more reliable RNA ligase coupling can be achieved using pre-activated nucleotide substrates.

The scientific literature documents that the adenylylated enzyme is unable to catalyze step 3 of the reaction. The addition of a small amount of 3',5'-(d)NDP, when using pre-activated nucleotide substrate, App(d)Np, is believed by the inventor to prevent RNA ligase from being irreversibly inactivated by the reverse reaction of step 2. Consequently, it is believed that the coupling reaction proceeds with greater efficiency. The addition of a small amount of pyrophosphate may perform the same function.

Pre-activated blocked nucleotides for use as substrates in the method of the invention can be conveniently synthesized in accordance with Example 1.

Other substrates which are coupled to the primer by the chain extending enzyme and which can be converted to an inert or slowly reacting product may also be employed.

DEBLOCKING ENZYMES

When the 3'-blocking group employed on the substrate is a phosphate group, the enzyme employed to remove the blocking group is a phosphatase. The principal function of the phosphatase is the irreversible removal of the 3'-phosphate blocking group from the extended primer (allowing subsequent RNA ligase coupling) and optionally, removal from the nucleotide substrate (preventing subsequent RNA ligase coupling). Careful selection of the phosphatase and the reaction conditions allows either: (1) dephosphorylation of both the extended primer and unreacted nucleotide substrate when substrate is not to be reused; or (2) dephosphorylation of only the extended primer when substrate is to be reused in the next cycle. Non-specific phosphatases such as Alkaline Phosphatase and Acid Phosphatase are useful when substrate reuse is not desired, as depicted in FIG. 2A; specific 3'-Phosphatases such as T4 3'-Phosphatase and Rye Grass 3'-Phosphatase are useful when substrate reuse is desired.

Alkaline Phosphatase will hydrolyze any monoester phosphate. Its high activity, especially at elevated temperatures, its substantial inability to degrade oligonucleotides, and its ability to be denatured irreversibly at 95° C. make it a useful deblocking enzyme in the invention. Alkaline phosphatase is readily available commercially from intestine and from bacteria. The inherent inorganic pyrophosphatase activity of alkaline phosphatase, not present in T4 3'-phosphatase, prevents a pyrophosphate build-up which may inhibit RNA ligase.

Acid Phosphatase has been isolated from wheat, potato, milk, prostate and semen, and catalyzes the same reactions as Alkaline Phosphatase. Acid Phosphatase can substitute for Alkaline Phosphatase if the pH of the reaction solution is acidic. Alkaline phosphatase is the preferred deblocking enzyme, however, when substrate is not to be reused in the next cycle.

The 3'-Phosphatases can be used either to dephosphorylate the primer selectively or to dephosphorylate both the primer and the nucleotide substrate depending on the reaction conditions selected. Low concentrations are used for selective dephosphorylation; high concentrations are used to dephosphorylate both.

The technical challenge of selective dephosphorylation is that it entails removal of the blocking group from the primer-blocked nucleotide product without removal of the blocking group from the unreacted blocked nucleotide substrate. In the method of the invention using RNA Ligase as the chain extending enzyme and AppNp as nucleotide substrate, the technical difficulty is selectively removing the 3'-phosphate blocking group of the extended primer, primer-pN-3'-phosphate, without removing the 3'-phosphate of the nucleotide substrate AppN-3'-phosphate. This difficulty is exacerbated by the fact that primer-pN-3'-phosphate and AppN-3'-phosphate are structurally identical with respect to the 3'-phosphate group in that they both share the same pN-3'-phosphate unit; the structural difference exists in a region distant from the 3'-phosphate, the component connected to the 5'-phosphate. This high degree of structural similarity would seemingly make discriminating between the substrates unachievable. Furthermore, the degree of discrimination (selectivity) must be sufficiently high to make a nucleotide substrate reuse technique useful. In the present invention, this challenge is solved as a result of the discovery that the enzyme 3'-Phosphatase is capable of achieving the selective dephosphorylation and that it does so in a manner which makes the invention useful.

3'-Phosphatase dephosphorylates only 2'- or 3'-phosphate esters. Two 3'-Phosphatases are commercially available: bacteriophage T4 and rye grass; both are useful in the method of the invention. The T4 enzyme is a bifunctional enzyme containing Polynucleotide Kinase and 3'-Phosphatase activities, catalyzed from two independent active sites. The T4 enzyme is commonly sold as "Polynucleotide Kinase". Since it is the 3'-phosphatase activity which is of main relevance in this invention, this enzyme herein will be referred to as T4 3'-Phosphatase. 3'-Phosphatase derived from rye grass is sold commercially as "3'-Nucleotidase" (Sigma Chemical, E. C. 3.1.3.6). This enzyme will also herein be referred to in this specification as 3'-Phosphatase. The method of the invention embodies any 3'-Phosphatase with the aforementioned substrate selectivity.

Genetic mutants of T4 3'-Phosphatase which lack associated kinase activity would also be useful in the invention. This task has already been described in the literature. A genetic mutant called pseT47 and a proteolytic fragment of the enzyme have the 3'-Phosphatase activity, but no kinase activity. Soltis et al., *J. Biol. Chem.* 257:11340–11345 (1982). Removal of the associated kinase activity may be desirable in preventing oligonucleotide circularization or polymerization. Other useful 3'-Phosphatases may be constructed by making genetic mutations which remove undesirable associated enzyme activities.

Given that 3'-Phosphatase is probably widespread in nature, it is anticipated that other 3'-Phosphatases derived from other sources will display similar or perhaps superior selective dephosphorylation and will also be useful in the invention. Thus far, experiments performed by the inventor have been unable to demonstrate that reuse of substrates can be applied to deoxyribose substrates AppdNp, since it appears that 3'-Phosphatase lacks the ability to selectively dephosphorylate primer-pdNp without substantially dephosphorylating AppdNp. A corresponding 2'-deoxy-3'-phosphatase with the aforementioned selectivity would be useful for AppdNp substrate reuse.

Special consideration is necessary for the method of FIGS. 3A and B to avoid significant co-incubation of 3'-phosphatase activity and RNA ligase activity in the presence of primer+AppNp, which may result in uncontrolled substrate addition. For example, RNA ligase may be heat inactivated after use, or using a thermostable enzyme, the RNA ligase activity can be temporarily turned off by lowering the temperature during the 3'-phosphatase incubation.

T4 3'-phosphatase has potential disadvantages with respect to its use in the synthesis of non-repeat regions of an oligonucleotide, as follows: (1) The 3'-phosphatase activity on unreacted nucleotide substrate is substantially slower than Alkaline Phosphatase; (2) AMP which is generated by the RNA ligase coupling reaction is not hydrolyzed by 3'-phosphatase and its accumulation after many coupling cycles may inhibit RNA ligase; and (3) associated kinase activity may result in cyclization or polymerization of the oligonucleotide if ATP is employed in the RNA ligase coupling reaction. Thus, while T4 3'-phosphatase is useful for all aspects of the method of the invention, the preferred Phosphatase for synthesis of non-repeat regions is Alkaline Phosphatase.

Other blocking groups which might be used in the method of the invention include blocking groups which are removed by light, in which case the addition of an enzyme to accomplish the unblocking would be unnecessary. See Ohtsuka et al, *Nucleic Acids Res*, 6(2):443–54 (1979). Other blocking groups include any chemical group covalently attached to the 2'- or 3'-hydroxyl of App(d)N-3'-OH, which can be removed without disrupting the remainder of the oligonucleotide. This may include esters, sulfate esters, glucose acetals, a heat labile group, or an acid or base labile group, which can be removed by incubation with esterases or proteases, sulfatases, glucosidases, heat, or acid or base, respectively.

ADDITIONAL METHOD STEPS

To synthesize long oligonucleotides, it is desirable to overcome two potential problems: the extension of the chain with unreacted nucleotide of the wrong type, and the subsequent extension of failed reaction products (unextended primer) from a previous cycle. These problems can be overcome by the addition of one or more additional enzymes to the basic scheme shown in FIG. 2A or 3A.

When synthesizing long oligonucleotides, such as about 25 bases or more, the unblocked nucleotide App(d)N concentration may build up to an extent that it couples to the primer at an unacceptable level, despite the fact that it is far less reactive than App(d)Np substrate. To minimize the incorporation of such residual nucleotides from previous reaction cycles, an additional enzyme can be added during, after or prior to the unblocking step which is effective to further degrade unreacted nucleotide substrate or nucleotide fragments into products that are no longer suitable substrates for RNA ligase.

A suitable enzyme for this purpose is a Dinucleotide Pyrophosphate Degrading Enzyme. Five distinct enzymes are capable of degrading App(d)N or App(d)Np, as described in the scientific literature:
(1) Nucleotide Pyrophosphatase (E. C. 3.6.1.9)
(2) Acid Pyrophosphatase (Tobacco, Sigma Chemical Co.)
(3) Diphosphopyridine Nucleosidase (E. C. 3.2.2.5)+ADP-Ribose Pyrophosphatase (E. C. 3.6.1.13)
(4) Dinucleotide Pyrophosphate Deaminase (Kaplan et al, *J. Biol. Chem.*, 194: 579–91 (1952))
(5) Dinucleotide Pyrophosphate Pyrophosphorylase (A. Kornberg, *J. Biol. Chem.*, 182: 779–93 (1950))

These enzymes are suitable for this invention because the degradation products are not substrates for RNA ligase. Among the Dinucleotide Pyrophosphate Degrading Enzymes, the preferred enzyme is Nucleotide Pyrophosphatase. This enzyme offers the following advantages: the reaction is irreversible, the enzyme degrades both App(d)N and App(d)Np; and nucleotide substrate is hydrolyzed to nucleosides+$PO_4$ when used with Alkaline Phosphatase. This is advantageous since nucleosides and phosphate are substantially non-inhibitory to all the enzymatic reactions of the method. Precipitation of nucleosides as a result of accumulation and poor solubility is probably beneficial by making the nucleosides inert to all reactions of the oligonucleotide synthesis, and by facilitating separation of the nucleosides from the final oligonucleotide product by centrifugation. The use of $App(d)N_1p(d)N_2p$ as a nucleotide substrate for RNA ligase requires the use of a Dinucleotide Pyrophosphate Degrading enzyme and Alkaline Phosphatase to achieve inactivation for use in the method.

Nucleotide Pyrophosphatase has been isolated from a great number of sources: human fibroblasts, plasmacytomas, human placenta, seminal fluid, *Haemophilus influenzae*, yeast, mung bean, rat liver, and potato tubers. The source with the best characterized enzymatic properties is potato tubers Bartkiewicz et al, *Eur. J. Biochem.*, 143:419–26 (1984). Bartkiewicz et al have shown that purified enzyme is capable of hydrolyzing dinucleotide pyrophosphates specifically, without hydrolyzing DNA or RNA. Nucleotide Pyrophosphatase isolated from snake venom is commercially available (Sigma Chemical Co.) and is the same enzyme as Phosphodiesterase I. (PDE-I) Accordingly, PDE-I can also be used to convert unreacted nucleotides into a form which does not serve as a substrate for RNA ligase, However, the exonuclease activity of the PDE-I warrants careful consideration since this activity may destroy the oligonucleotide product and prior art does not teach the use of exonucleases in a synthetic method.

The second potential difficulty with the method of the invention arises from a build up of failure sequences due to incomplete RNA ligase coupling. The RNA ligase coupling reaction can be substantially optimized kinetically in accordance with the invention. Dithiothreitol and TRITON X-100 (octylphenoxy polyethoxy ethanol) greatly stimulate RNA ligase activity. Nevertheless, even under optimized conditions, the coupling reaction is not 100% efficient, resulting in primer chains which have not been coupled to the blocked nucleotide. If not removed, these unreacted primer chains will still be able to couple with nucleotide in the next coupling cycle. This will result in the accumulation of (n–1) failure sequences in the final product mix. Two independent solutions have been devised by the inventor to solve this problem: Exonuclease treatment and Enzymatic Capping.

An exonuclease can be added after RNA ligase coupling to hydrolyze uncoupled primer chains to (d)NMP's. The Exonuclease can be utilized before, after, or concurrently with the dinucleotide pyrophosphate degrading enzyme. The Exonuclease used for this purpose should have the following properties:

(1) hydrolyzes oligonucleotides in the 3' to 5' direction; and (2) hydrolyzes specifically oligonucleotides with a free terminal 3'-hydroxyl group and is substantially unable to hydrolyze oligonucleotides which are blocked at the 3'-end.

Primer chains which fail to couple during incubation with RNA ligase differ from primer chains which do couple. Uncoupled primers have a 3'-hydroxyl terminus; coupled primers have a blocked 3'-phosphate. Therefore, as a result of the selectivity of the Exonuclease, only uncoupled primer chains are degraded to (d)NMP's. Exonuclease incubation should be performed prior to incubation with Phosphatase, and exonuclease activity should not be present during phosphatase incubation. Otherwise, oligonucleotide product will be hydrolyzed.

Three enzymes satisfy these criteria and are suitable as Exonuclease in this invention: Exonuclease I (*E. coli*), Phosphodiesterase I (snake venom), and Polynucleotide Phosphorylase. Phosphodiesterase I hydrolyzes both oligoribonucleotides and oligodeoxyribonucleotides; Exonuclease I is substantially specific for oligodeoxyribonucleotides (although it has been used successfully on mixed deoxyribose/ribose oligonucleotides); Polynucleotide Phosphorylase is substantially specific for oligoribonucleotides. TRITON X-100 and dithiothreitol have been observed experimentally by the inventor to stimulate the activity of Exonuclease I and PDE-I.

PDE-I offers two advantages: (1) PDE-I hydrolyzes both oligoribonucleotides and oligodeoxyribonucleotides, making it useful for the synthesis of both, and (2) PDE-I has nucleotide pyrophosphatase activity. Although PDE-I requires careful control of enzymatic reaction conditions to avoid degrading primer chains blocked by a 3'-phosphate, conditions can be achieved to hydrolyze all 3'-hydroxyl primer chains and all unreacted blocked nucleotide substantially without hydrolyzing 3'-phosphate primer chains. Given that it is advantageous to use a Dinucleotide Pyrophosphate Degrading activity and an Exonuclease activity simultaneously, snake venom PDE-I provides two functions for the price of one enzyme.

Figure 2B:
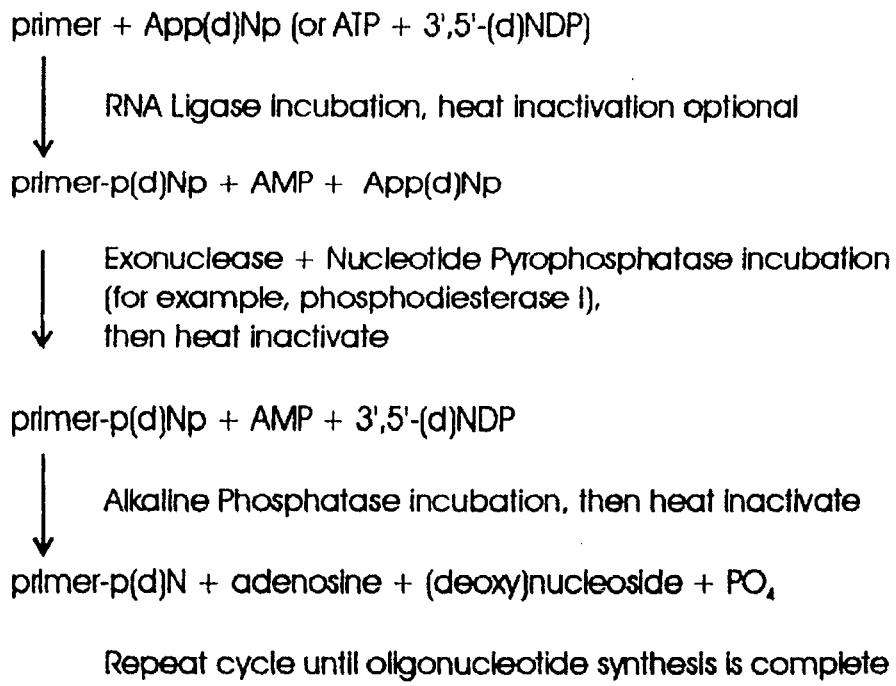

The combination of these two modifications of the Basic method results in the Preferred method for the synthesis of oligonucleotides, outlined in FIGS. 2B and 3B. The power of this method is exemplified in Example 5. ApApCpdApdA is synthesized by two coupling cycles with the activated nucleotide AppdAp and ApApCp initial primer. Thin layer chromatography demonstrated that the reaction mixture at the end of the synthesis contained only the oligonucleotide ApApCpdApdA and the nucleosides adenosine and deoxyadenosine. The mixture was devoid of traces of n−1 and n−2 failure sequences. Due to the enormous size difference between the n-mer oligonucleotide product and the nucleosides, the oligonucleotide product can be easily purified. Furthermore, an application may not require removal of the nucleosides.

As mentioned earlier, another technique can be used to remove uncoupled primer chains, denoted herein as "Enzymatic Capping." After the RNA ligase coupling reaction, unreacted primer chains can be capped with a chain terminating nucleotide catalyzed by a transferase enzyme. The capped chains are no longer substrates for coupling with RNA ligase in subsequent coupling cycles. Primer chain termination can be achieved with Terminal deoxynucleotidyl Transferase+dideoxynucleoside triphosphate or with RNA ligase+AppddN (the dideoxy analog of AppdN). Chain terminated failure sequences can be subsequently hydrolyzed to nucleotides using an exonuclease as described above. One potential disadvantage of the enzymatic capping technique is the coupling efficiency of the chain terminating step. If the coupling efficiency is low, then (n−1) failure sequences will be present in the final solution mixture. Thus, the favored method for removing uncoupled primer chains is the Exonuclease method discussed earlier.

REMOVAL OF AMP

AMP generated during the coupling reaction may inhibit the forward coupling reaction or participate in the reverse coupling reaction. In accordance with the invention, this can be avoided by the addition of an enzyme or enzyme combination which degrades AMP to a less inhibitory form. For the purpose of this invention, an AMP Inactivating Enzyme or Enzyme Combination, is defined as an enzyme or enzyme combination which converts Adenosine 5'-Monophosphate (AMP) to a less reactive form, i.e., to a form which is less inhibitory to the forward coupling reaction catalyzed by RNA Ligase, or which is less able to participate in the reverse coupling reaction catalyzed by RNA Ligase, or which assists in driving (thermodynamically or kinetically) the forward coupling reaction catalyzed by RNA Ligase. An AMP Inactivating Enzyme or Enzyme Combination is useful in making the RNA Ligase coupling reaction faster, more efficient, or more reliable, by converting AMP, generated by the forward coupling reaction, to a form with diminished undesirable properties.

Several AMP Inactivating Enzymes have been devised by the inventor. These enzymes are preferably used concurrently with RNA Ligase incubation since they do not substantially degrade primer, extended primer product, or App-(d)Np substrate. These enzymes can be present or can be used at any or all steps of a cycle since their activity is not deleterious to the One Pot method. Such enzymes include:

(1) 5'-Nucleotidase (E. C. 3.1.3.5):

$AMP+H_2O \rightarrow Adenosine+phosphate$ (2) AMP Nucleosidase (E. C. 3.2.2.4):

$AMP+H_2O \rightarrow Adenine+ribose-5-phosphate$ (3) AMP Deaminase (E. C. 3.5.4.6):

$AMP+H_2O \rightarrow Inosine-5'-phosphate+NH_3$

Figure 8:
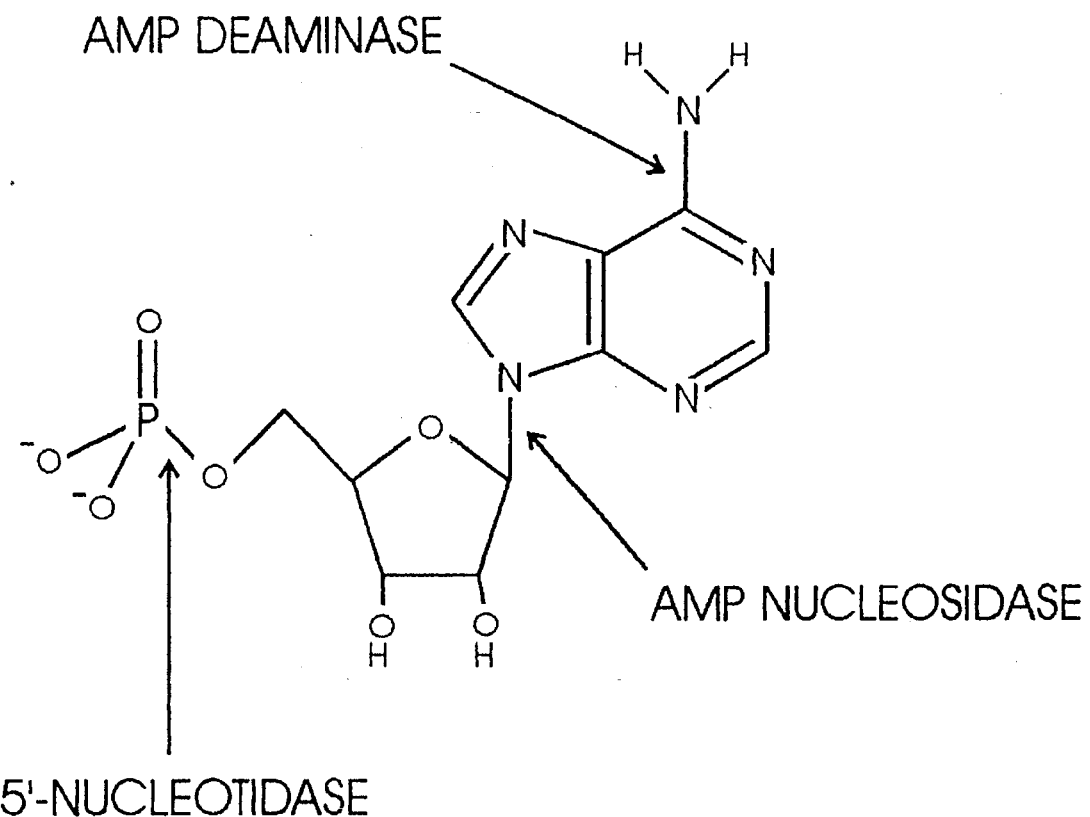
FIG. 8: The structure of AMP and the cleavage points of various enzymes.

For clarity, FIG. 8 shows the structure of AMP and the location of the covalent bond broken by the hydrolytic activity of each enzyme. Experiments by the inventor strongly suggest that the hydrolytic products of these enzymes are less inhibitory to RNA Ligase than AMP. Furthermore, it is strongly suspected that these hydrolytic products are unable to participate in the reverse RNA Ligase coupling reaction. Example 19 demonstrates the use of these enzymes.

These three enzymes using AMP substrate may be combined in a rational manner with other enzymes, which further convert their products to even less reactive products, to create an AMP Inactivating Enzyme Combination. Such enzymes include:

(1) Adenosine Nucleosidase (E. C. 3.2.2.7):

$Adenosine+H_2O \rightarrow Adenine+ribose$ (2) Adenosine Deaminase (E. C. 3.5.4.4):

$Adenosine+H_2O \rightarrow Inosine+NH_3$ (3) Nucleoside Phosphorylase (E. C. 2.4.2.1):

Adenosine+PO$_4$→ribose-1-phosphate+Adenine

Example 19 demonstrates the enzyme combination 5'-Nucleotidase+Adenosine Deaminase. Other potentially useful combinations, such as 5'-Nucleotidase+Adenosine Nucleosidase, can be constructed by identifying the side product which one wishes to convert to a less reactive form and consulting *Enzyme Nomenclature* (Academic Press, 1992) or the scientific literature to locate an enzyme which effects the conversion. For example, to remove adenine., consultation with *Enzyme Nomenclature* discloses the enzyme Adenine Deaminase (E. C. 3.5.4.2) which converts adenine to hypoxanthine, which may be suitable for inclusion in an enzyme combination. Similarly, uridine can be converted to uracil by adding Uridine Nucleosidase (E. C. 3.2.2.3).

AMP Nucleosidase and AMP Deaminase are reported in the literature as allosterically activated by ATP and allosterically inactivated by phosphate. Experiments indicate that these enzymes have adequate activity in the absence of ATP and under the conditions employed for oligonucleotide synthesis demonstrated in Example 19. A thermostable version is probably obtainable from a thermophilic organism, e.g. *Thermus aquaticus, Pyrococcus,* etc and would be useful in the method since replenishment would be unnecessary.

The concept of an AMP Inactivating Enzyme or Enzyme Combination as a useful technique in the method of the invention is not limited to the enzymes disclosed in this specification, but shall include any enzyme which can be implemented for the previously stated purpose. Such enzymes may already be described in the literature, may be discovered in the future, or may be a man-made genetic modification of a known AMP Inactivating Enzyme. For example, a mutant of either AMP Nucleosidase or AMP Deaminase with constitutively high activity would be useful. Many examples exist in the literature in which mutations affect allosteric enzyme properties.

SUPPLEMENTAL TECHNIQUES

While the foregoing describes the basic aspects of the claimed invention, it will be appreciated that numerous modifications are possible without departing from the basic invention.

In practicing the method of the invention, enzyme inactivation where needed can be readily accomplished using heat or by proteolysis with a protease, e.g., proteinase K. Protease can be subsequently inactivated by heat or by chemical inhibitor such as phenylmethylsulfonyl chloride.

Proteolysis with proteinase K can also be used to hydrolyze the denatured protein debris, which accumulates as a result of heat inactivation of enzymes, to small soluble peptides. Although the debris is inert, its accumulation after many cycles may pose a viscosity problem for mixing or pipetting operations. The proteolytic digestion may be enhanced by the addition of TRITON X-100. Physical methods for removing the debris such as filtration, ultrafiltration, centrifugation, and extraction with organic solvents such as phenol and chloroform can also be utilized, but are not readily automated and are more appropriate as an option at the end of the synthesis.

The method of the invention is particularly well adapted to the synthesis of oligoribonucleotides. It can also be used to synthesize oligodeoxyribonucleotides, although coupling times will be longer and coupling efficiencies will be lower. For most applications an oligoribonucleotide can substitute for an oligodeoxyribonucleotide with equal effectiveness. Oligoribonucleotides can be used as hybridization probes, as primers for dideoxy DNA sequencing (RNase can remove the primer prior to electrophoresis); as primers for the polymerase chain reaction using a thermostable reverse transcriptase; and as probes for the ligase chain reaction.

For applications which have an absolute requirement for oligodeoxyribonucleotides, an oligoribonucleotide may be converted to its complementary oligodeoxyribonucleotide. The oligoribonucleotide can be synthesized with a hairpin at the 3'-end, allowing priming for reverse transcriptase, and subsequent RNase H digestion.

Large scale manufacture of enzymes employed in the present invention having suitable purity may be accomplished by established methods for expression of recombinant protein in an overproducing organism. One such technique is to manufacture the enzymes as fusion proteins with an affinity protein, allowing purification in one step by affinity chromatography. As the activity of many enzymes is not affected by the presence of the affinity protein, proteolytic removal of the affinity protein is probably not necessary.

Alternative embodiments of the present invention may be implemented to reduce the cost of enzymes. For example, instead of inactivating the enzymes by heat or proteolysis, enzymes may be recovered from the oligonucleotide solution by passing the solution through an enzyme-binding solid support, such as an affinity chromatography column, and then optionally reused in later cycles of the invention. Alternatively, enzymes may be covalently attached to a solid support matrix and placed in columns. The method of the invention is then performed by pumping solutions through the appropriate columns.

The hydrolysis of phosphate anhydrides by Alkaline Phosphatase and Nucleotide Pyrophosphatase, and the hydrolysis of phosphodiesters by Exonuclease releases an equivalent of acid. Preventing an unacceptable drop in pH, especially for long oligonucleotides, may entail the occasional addition of base or the use of a higher buffer concentration.

Phosphate concentrations exceeding about 20 mM at pH 8.0 and 10 mM MgCl$_2$ may eventually precipitate the magnesium. This is deleterious since magnesium is a required cofactor for many of the enzymes in the One Pot method. This problem can be solved by conducting the synthesis at pH 7.0. Experiments confirm that no precipitation of MgPO$_4$ is observed in a solution of 10 mM MgCl$_2$ and 250 mM PO$_4$ at pH 7.0. Alternatively, phosphate can be removed by precipitation out of solution by adding an excess of Mg$^{++}$, Ca$^{++}$, Al$^{+++}$ or other cationic species which forms an insoluble phosphate salt. Hydrolysis of pyrophosphate by Inorganic Pyrophosphatase prevents precipitation of magnesium pyrophosphate, which is highly insoluble in aqueous solutions.

Growth in the reaction mixture of microorganisms may result in the secretion of nucleases which could degrade the nucleotides and oligonucleotides. This problem is minimized by the frequent heat inactivation steps which sterilize the reaction solution and the use of the detergent TRITON X-100 which may hinder most microbes. Alternatively, microbial growth inhibitors, such as glycerol, EDTA, sodium azide, merthiolate, or antibiotics may be added to the reaction solution. A useful growth inhibitor for the method of the invention should not significantly inhibit the enzymatic reactions in the synthesis of the oligonucleotide. No significant inhibition of RNA ligase was observed by the inventor in the presence of 0.1% sodium azide and 0.1% merthiolate.

Inadvertent nuclease contamination of the synthesis reaction can be countered by adding a nuclease inhibitor or adding protease intermittently. Numerous RNase inhibitors are described in the literature,. including RNase Inhibitor Protein (human placenta) and Vanadyl Ribonucleoside Complexes (Sigma Chemical Co). No significant inhibition of RNA ligase was observed by the inventor in the presence of 0.1 mM vanadyl ribonucleoside complexes.

Evaporative loss can be minimized by reducing the temperature or duration of the heat inactivation steps or by overlaying the aqueous phase with light mineral oil. For example, snake venom PDE-I can be inactivated by heating at 50° C. for 5 minutes; commercially available heat labile alkaline phosphatase from Arctic fish can be inactivated at 65° C.

Consumption of dithiothreitol, or other reducing agents, that stimulate the activity of the enzymes used in the One Pot method by oxidation may be solved by either intermittent replenishment or by conducting the synthesis in an oxygen-free environment.

The formation of secondary structure in an oligonucleotide may block enzymatic access to the 3'-end of the oligonucleotide. Several measures may be taken. The oligonucleotide can be synthesized as several smaller pieces which do not self anneal and then ligated together with RNA ligase. Alternatively, the base portion of a nucleotide can be modified with protecting groups such as acetyl groups which prevents base pairing. The protecting groups are removed at the end of the synthesis. A third alternative is the addition of denaturants to the reaction mixture which disrupt oligonucleotide base pairing without substantially inhibiting the enzymatic reactions. Suitable denaturants include dimethyl sulfoxide, formamide, methylmercuric hydroxide and glyoxal. No significant inhibition of RNA ligase was observed by the inventor in the presence of 20% dimethyl sulfoxide.

APPARATUS

The minimal configuration for an apparatus which is useful for synthesizing oligonucleotides by the method of the invention is: (1) at least one vessel containing reaction solution for performing the synthesis of an oligonucleotide, (2) means for controlling the temperature of the reaction solution(s), (3) means for separately supplying at least four different blocked nucleotide feed stocks to the solution(s), (4) means for supplying at least one enzyme feed stock to the solution(s), and (5) means for controlling the sequential addition of blocked nucleotide feed stocks and enzyme feed stock(s) to the solution(s). Two separate embodiments of the minimal configuration are described.

Figure 9:
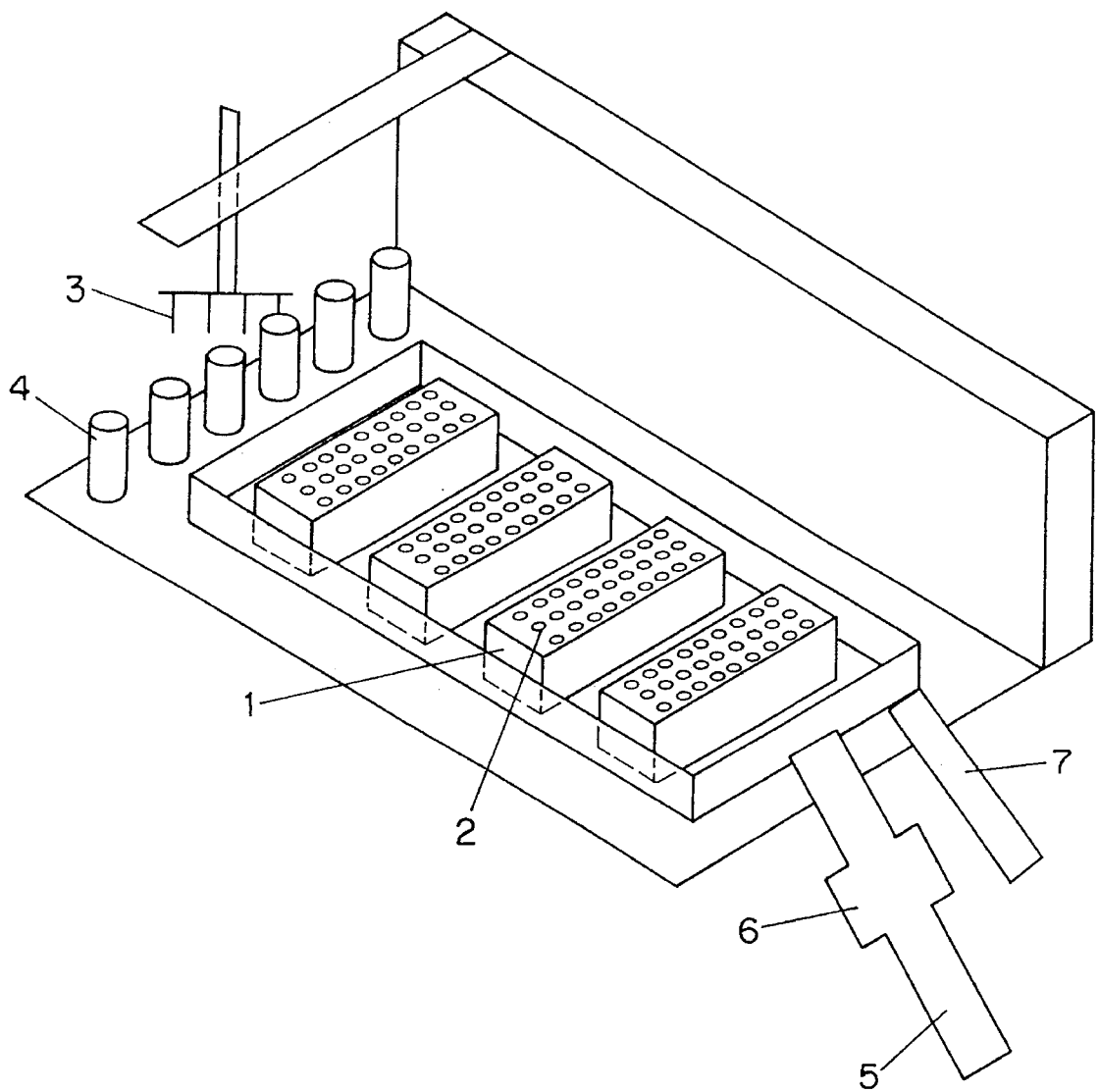
FIG. 9: Apparatus for practicing the method of the invention, suitable for synthesizing many oligonucleotides simultaneously.

FIG. 9 shows an apparatus which can be used in the practice of the invention for synthesizing many oligonucleotides simultaneously. The apparatus has a plurality of reaction vessels in the form of wells 2 drilled in a metal block 1. At least four different blocked nucleotide feed stocks and at least one enzyme feed stock are provided from reagent bottles 4 using one or several liquid handling robots 3. The temperature of the block can be increased by turning on a heating element (not shown) beneath the block and can be lowered by opening a valve 6 which allows water 5 to flow through a cavity (not shown) underneath the block and then exit 7. A computer (not shown) controls the sequential addition of blocked nucleotides and enzyme(s) to the vessels and controls the temperature of the block.

This apparatus can be further improved by providing a separate means for mixing the synthesis reaction solutions without the need for the robotic liquid dispensing system to mix reaction solutions. This can be accomplished by placing a magnetic stir bar or many small magnetic or paramagnetic particles in each of the wells in active use, and agitating the stir bars with a moving magnetic field. Wells may be coated with an inert material to avoid heavy metal contamination.

Figure 10:
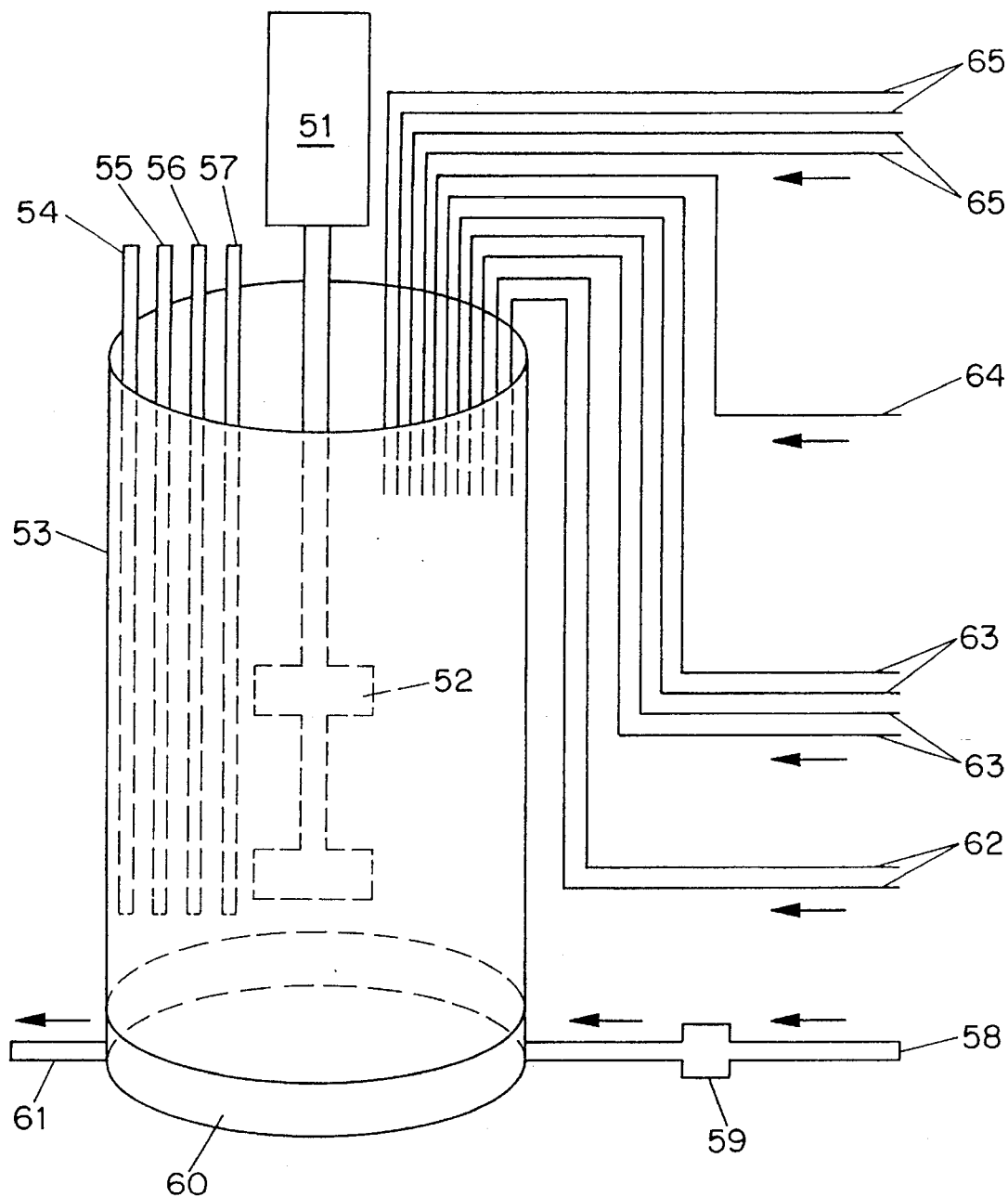
FIG. 10: Apparatus for practicing the method of the invention, suitable for the bulk synthesis of an oligonucleotide.

FIG. 10 shows an apparatus which can be used in the practice of the invention for synthesizing a single oligonucleotide in bulk quantity. It consists of a single large vessel 53 for the synthesis reaction which is mixed by a stirring device. The stirring device may be a motor 51 connected to a rotating impeller 52, or alternatively a large stir bar (not shown) rotated by a magnetic stirrer (not shown). The temperature of the reaction solution is increased with a heating device 54 or a heating element (not shown) located inside cavity 60, and lowered by opening a valve 59 which allows cool water 58 to flow into a cavity 60 beneath the vessel and then exit 61 the cavity. The four blocked nucleotide feed stocks 63 are added to the vessel either by four separate pumps (not shown) or by a single pump with a valve controlling connection of the feed stocks to the pump (not shown). At least one enzyme feed stock 64 can be added in the same manner. A computer (not shown) controls the sequential addition of blocked nucleotides and enzyme(s) to the vessel and controls the temperature of the solution.

Additional components could enhance the performance of the bulk scale synthesizer. Ancillary feed stocks 65 for additional blocked nucleotides, enzymes, or other reagents can be added. The temperature of the reaction solution is monitored by a temperature probe 55. A pH probe 56 monitors the reaction solution pH and acid or base feed stocks 62 can be added as necessary to maintain pH as desired. An inert gas such as nitrogen is slowly added via tube 57 to the reaction solution to remove oxygen (which can be monitored by an oxygen electrode). A computer (not shown) can control the apparatus, receiving inputs of solution temperature, pH, and sending outputs to control the addition of feed stocks (blocked nucleotide feed stocks, enzyme feed stock(s), acid, base, and ancillary reagents), heating device, cooling valve 59, nitrogen purge rate, and motor rotation speed. Nucleoside and phosphate by-products may be reduced by adding a dialysis or ultrafiltration system (not shown).

Reagents

Several reagents useful in the practice of the invention have not been previously described, and these reagents are an aspect of the present invention. In particular, the activated deoxyribonucleotides AppdAp, AppdGp and AppdCp; and dinucleotides of the general formula $App(d)N_1p(d)N_2p$, wherein $N_1$ and $N_2$ are any nucleosides.

The activated deoxyribonucleotides can be synthesized by phosphorylation of the 5'-hydroxyl of the corresponding 3'-dNMP using phosphatase free polynucleotide kinase and ATP, to yield 3',5'-dNDP. This is then activated in accordance with Example 1.

The dinucleotides can be synthesized in several steps. First, $(d)N_1p(d)N_2p(d)N_3$ is synthesized chemically, for example using the phosphoramidite method. This product is then phosphorylated using ATP and Polynucleotide Kinase to yield $p(d)N_1p(d)N_2p(d)N_3$. The enzyme is then inactivated. The phosphorylated material is then partially digested, e.g. using RNase, DNase or a nuclease to yield p(d)$N_1$p(d)$N_2$p. The enzyme activity is then removed using protease followed by heat, after which the material is activated as in Example 1. Activation of such dinucleotides substrates is greatly accelerated by the presence of a primer.

While the method of invention can be described in terms of a cycle of steps which result in synthesis of oligonucleotides, certain aspects of the invention are independently viewed as part of applicant's inventive concept. For example, the application of an exonuclease to degrade any oligonucleotide primer which was not extended is a useful improvement in the context of any method for synthesizing an oligonucleotide, wherein an oligonucleotide primer is extended coupling a blocked nucleotide to the 3'-end of the primer, wherein primer-blocked nucleotide product is resistant to exonuclease attack. Similarly, the application of a transferase enzyme and a chain terminating nucleotide, whereby any oligonucleotide primer which was not extended is end-capped to render it unreactive to further extension in any method for synthesizing an oligonucleotide is a useful improvement in the context of any method for synthesizing an oligonucleotide wherein an oligonucleotide primer in a reaction mixture is extended by coupling a blocked nucleotide to the 3'-end of the primer, such that primer-blocked nucleotide product is formed that is unreactive with the transferase enzyme.

The method will now be further described by way of the following, non-limiting examples.

EXAMPLE 1

Enzymatic Synthesis of AppAp and AppdAp

The synthesis of activated nucleotides, App(d)Np and App(d)Np(d)Np can be performed enzymatically using RNA ligase Inorganic Pyrophosphatase. This example demonstrates the synthesis of AppAp and AppdAp; other activated nucleotides can be synthesized in the same manner.

The following solution in a total volume of 300 ul was placed in an ependorf tube: 50 mM Tris-Cl, pH 8.0, 10 mM $MgCl_2$, 10 mM Dithiothreitol (DTT), 0.1% TRITON X-100, 11 mM 3',5'-ADP, 10 mM ATP, 0.1 units Inorganic Pyrophosphatase (yeast, Sigma Chemical Co.), 80 units RNA ligase (phage T4, New England Biolabs). For the synthesis of AppdAp, 3',5'-dADP was used in place of 3',5'-ADP. This solution was incubated at 37° C. for 40 hours. RNA ligase was heat inactivated at 95° C. for 5 minutes. Residual ATP was removed by adding 2 units Hexokinase (yeast, Sigma Chemical Co.)+15 ul 200 mM glucose and incubating at 37° C. for 1 hour. Hexokinase was heat inactivated at 95° C. for 5 minutes. The solution was cooled to room temperature and pelleted at 12,000 g for 1 minute to remove the insoluble protein debris. This final product was analyzed by thin layer chromatography on silica using isobutyric acid:concentrated ammonium hydroxide:water at 66:1:33 containing 0.04% EDTA (hereinafter "butyric-TLC"). No ATP was detected; the major product was App(d)Ap with a small amount of 3',5'-ADP present. AppAp and AppdAp prepared in this manner were used in all the following examples.

EXAMPLE 2

One Pot Synthesis of ApApCpApA

The following solution was placed in a total volume of 40 ul in an ependorf tube: 50 mM Tris-Cl, pH 8.0, 10 mM $MgCl_2$, 10 mM DTT, 0.1% TRITON X-100, 1 mM ApApC primer, 5 mM AppAp. The following procedures were performed:

cycle 1
(a) Add 2 ul (40 units) RNA ligase (phage T4, New England Biolabs). Incubate at 37° C. for 15 minutes. Heat at 95° C. for 5 minutes, cool to room temperature.
(b) Add 1 ul (3 units) Alkaline Phosphatase (calf intestine, US Biochemicals). Incubate at 37° C. for 30 minutes. Heat at 95° C. for 5 minutes, cool to room temperature.
cycle 2 - starting volume is 20 ul
(a) Add 10 ul 10 mM AppAp+1 ul RNA ligase. Incubate at 37° C. for 30 minutes. Heat at 95° C. for 5 minutes, cool to room temperature.
(b) same as cycle 1

Insoluble coagulated protein-debris was removed by pelleting at 12,000 g for 1 min. The reaction mixture supernatant was analyzed by thin layer chromatography using the SureCheck™ Oligonucleotide Kit (US Biochemicals)(hereinafter "USB TLC"). The only oligonucleotide product visible on the TLC plate was the desired oligonucleotide product ApApCpApA; i.e., no n−2, n−1, n+1, n+2, etc. products were formed. This experiment demonstrates that AppA does not participate in the RNA ligase coupling reaction, due to its slow coupling rate relative to AppAp. This experiment also demonstrates that coupling times with efficiencies approaching 100% can be achieved in 15 minutes under these experimental conditions. This is attributable to the nucleotide 3',5'-ADP present in the AppAp preparation, which prevents covalent inactivation of RNA ligase. The final yield of oligonucleotide product approached 100%.

EXAMPLE 3

Synthesis of (ApApC)-pApA

The following solution was placed in a total volume of 30 ul in an ependorf tube: 50 mM Tris-Cl, pH 8.0, 10 mM $MgCl_2$, 10 mM DTT, 0.1% TRITON X-100, 1 mM ApApC primer, 5 mM AppAp. The following procedures were performed:

cycle 1
(a) Add 1 ul (20 units) RNA ligase (phage T4, New England Biolabs). Incubate at 37° C. for 1 hour. Heat at 95° C. for 5 minutes, cool to room temperature.
(b) Add 1 ul (0.03 units) Nucleotide Pyrophosphatase (snake venom, Sigma Chemical Co. P7383). Incubate at 37° C. for 30 minutes. Heat at 95° C. for 5 minutes, cool to room temperature.
(c) Add 1 ul (3 units) Alkaline Phosphatase (calf intestine, US Biochemicals). Incubate at 37° C. for 30 minutes. Heat at 95° C. for 5 minutes, cool to room temperature.
cycle 2
(a) Add 10 ul 10 mM AppAp+1 ul RNA ligase. Incubate at 37° C. for 5 hours. Heat at 95° C. for 5 minutes, cool to room temperature.
(b) same as cycle 1
(c) same as cycle 1
Insoluble coagulated protein debris was removed by pelleting at 12,000 g for 5 min. USB TLC revealed pure ApApCpApA product with no visible n−1 or initial primer present. The yield of final product was about 90% of the initial primer.

EXAMPLE 4

Synthesis of (ADApC)-pADA

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppAp. The following procedures were performed:

cycle 1

Performed identically to cycle 1 of example 3.

cycle 2

(a) Add 1.5 ul 100 mM ATP+3 ul 50 mM 3'5'-ADP+0.1 units Inorganic Pyrophosphatase+1 ul RNA ligase. Incubate at 37° C. for 5 hours. Heat at 95° C. for 5 minutes, cool to room temperature.

(b) same as cycle 1 of example 3

(c) same as cycle 1 of example 3

Insoluble coagulated protein debris was removed by pelleting at 12,000 g for 5 min. USB TLC revealed nearly pure ApApCpApA product with no visible n−1 or initial primer present. The yield of final product was about 90% of the initial primer.

EXAMPLE 5

Synthesis of dApdA

The oligonucleotide dApdA was synthesized by initially synthesizing the oligonucleotide (ApApC)-pdApdA using the initial primer ApApC and two coupling cycles with the activated nucleotide AppdAp. Synthesized oligodeoxyribonucleotide dApdA was cleaved from the initial primer using RNase treatment.

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppdAp. The following procedures were performed:

cycle 1

(a) Add 1 ul (20 units) RNA ligase (phage T4, New England Biolabs). Incubate at 37° C. for 3 hours. Heat at 95° C. for 5 minutes, cool to room temperature.

(b) Add 1 ul (0.03 units) Nucleotide Pyrophosphatase (snake venom, Sigma P7383). Incubate at 37° C. for 30 minutes. Heat at 95° C. for 5 minutes, cool to room temperature.

(c) Add 1 ul (3 units) Alkaline Phosphatase (calf intestine, US Biochemicals). Incubate at 37° C. for 30 minutes. Heat at 95° C. for 5 minutes, cool to room temperature.

cycle 2

(a) Add 10 ul 10 mM AppdAp+1 ul RNA ligase. Incubate at 37° C. for 20 hours. Heat at 95° C. for 5 minutes, cool to room temperature.

(b) same as cycle 1

(c) same as cycle 1

Insoluble coagulated protein debris was removed by pelleting at 12,000 g for 5 min. USB TLC revealed pure ApApCpdApdA product with no visible n−1 or initial primer present. The yield of final product was about 90% of the initial primer. Cleavage of the synthesized oligodeoxyribonucleotide dApdA from the oligonucleotide product was performed by adding 100 ng RNase A (bovine pancreas, US Biochemicals) to 4 ul oligonucleotide product and incubating at 37° C. for 1 hour. dApdA product was analyzed and purified from nucleosides and ApApCp using butyric TLC.

EXAMPLE 6

Synthesis of (ApApC)-pApA

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppAp containing 10% glycerol as a preservative. The solution was overlaid with 50 ul light mineral oil to prevent evaporation. The following procedures were performed:

cycle 1

(a) Add 1 ul (20 units) RNA ligase (phage T4, New England Biolabs)+0.5 ul (0.2 units) Inorganic Pyrophosphatase (Sigma, yeast)+0.5 ul (0.025 units) 5'-Nucleotidase (Sigma, snake venom). Incubate at 37° C. for 1 hour. Heat at 95° C. for 5 minutes, cool to room temperature.

(b) Add 1 ul (0.03 units) Nucleotide Pyrophosphatase (Sigma P7383, snake venom). Incubate at 37° C. for 30 minutes. Heat at 95° C. for 5 minutes, cool to room temperature.

(c) Add 1 ul (3 units) Alkaline Phosphatase (calf intestine, US Biochemicals)+0.5 ul (0.05 units) Nucleoside Phosphorylase (Sigma). Incubate at 37° C. for 30 minutes. Heat at 95° C. for 5 minutes, cool to room temperature.

cycle 2

(a) Add 10 ul 10 mM AppAp+1 ul (20 units) RNA ligase. Incubate at 37° C. for 5.5 hours. Heat at 95° C. for 5 minutes, cool to room temperature.

(b) same as cycle 1

(c) same as cycle 1

Insoluble coagulated protein debris was removed by adding 5 ug proteinase K (Sigma) and incubating at 60° C. for 5 minutes. This treatment removed most of the debris. The proteinase K was heat inactivated at 95° C. for 5 minutes, then cooled to room temperature. Mineral oil was removed with a pipettor. Residual mineral oil was removed by adding 100 ul chloroform, vortexed vigorously, and centrifuged at 12,000 g for 1 minute to separate the phases. The chloroform extraction also removed protein from the aqueous phase, which appeared between the two phases. The upper aqueous phase was collected by pipettor and was analyzed by USB TLC. This revealed pure ApApCpApA product with no visible n−1 or initial primer present. The yield of final product was about 90% of the initial primer.

EXAMPLE 7

Synthesis of (ApApC)-pApA

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppAp. The following procedures were performed:

cycle 1.

(a) Add 1 ul (20 units) RNA ligase (phage T4, New England Biolabs). Incubate at 37° C. for 1 hour. Add 1 ug Proteinase K (Sigma), incubate at 60° C. for 5 minutes, heat at 95° C. for 5 minutes to inactivate protease, and cool to room temperature.

(b) Add 1 ul (0.03 units) Nucleotide Pyrophosphatase (snake venom, Sigma P7383). Incubate at 37° C. for 30 minutes. Add 1 ug Proteinase K (Sigma), incubate at 60° C. for 5 minutes, heat at 95° C. for 5 minutes to inactivate protease, and cool to room temperature.

(c) Add 1 ul (3 units) Alkaline Phosphatase (calf intestine, US Biochemicals). Incubate at 37° C. for 30 minutes. Add 1 ug Proteinase K (Sigma), incubate at 60° C. for 5 minutes, heat at 95° C. for 5 minutes to inactivate protease, and cool to room temperature.

cycle 2

(a) Add 10 ul 10 mM AppAp+1 ul (20 units) RNA ligase. Incubate at 37° C. for 5.5 hours. Add 1 ug Proteinase K (Sigma), incubate at 60° C. for 5 minutes, heat at 95° C. for 5 minutes to inactivate protease, and cool to room temperature. (b) same as cycle 1
(c) Add 1 ul (3 units) Alkaline Phosphatase (calf intestine, US Biochemicals). Incubate at 37° C. for 30 minutes. The use of Proteinase K for the inactivation of enzymes after each step prevented the accumulation of insoluble coagulated protein debris. USB TLC revealed pure ApApC-pApA product with no visible n–1 or initial primer present. The yield of final product was about 90% of the initial primer.

EXAMPLE 8

Synthesis of (ApApC)-pApA

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppAp, containing 10% dimethylsulfoxide to inhibit base pairing. The synthesis procedure was identical to Example 3. USB TLC revealed pure-ApApCpApA product with no visible n–1 or initial primer present. The yield of final product was about 90% of the initial primer.

EXAMPLE 9

Synthesis of (ApApC)-pApA

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppAp, 10 uM Vanadyl Ribonucleoside Complexes (to inhibit any contaminating RNases). The synthesis procedure was identical to Example 3. USB TLC revealed pure ApApCpApA product with no visible n–1 or initial primer present. The yield of final product was about 90% of the initial primer.

EXAMPLE 10

Synthesis of (ApApC)-pApA

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, and 5 mM AppAp. The following procedures were performed:
cycle 1
(a) Add 1 ul (20 units) RNA ligase (phage T4, New England Biolabs)+1 ul 3 mM sodium pyrophosphate+1 ul 300 mM glucose+0.2 units hexokinase (yeast, Sigma). Incubate at 37° C. for 1 hour. Heat at 95° C. for 5 minutes, cool to room temperature.
(b) Add 1 ul (0.03 units) Nucleotide Pyrophosphatase (snake venom, Sigma P7383). Incubate at 37° C. for 30 minutes. Heat at 95° C. for 5 minutes, cool to room temperature.
(c) Add 1 ul (3 units) Alkaline Phosphatase (calf intestine, US Biochemicals). Incubate at 37° C. for 30 minutes. Heat at 95° C. for 5 minutes, cool to room temperature.
cycle 2
(a) Add 10 ul 10 mM AppAp+1 ul (20 units) RNA ligase+1 ul 3 mM sodium pyrophosphate+1 ul 300 mM glucose+ 0.2 units hexokinase. Incubate at 37° C. for 3.5 hours. Heat at 95° C. for 5 minutes, cool to room temperature.
(b) same as cycle 1
(c) same as cycle 1
Insoluble coagulated protein debris was removed by pelleting at 12,000 g for 5 min. USB TLC revealed nearly pure ApApCpApA product with slight n–1 side product.

EXAMPLE 11

One Pot Synthesis of ApApC-pApA with TAP

The following solution was placed in a total volume of 30 ul in an ependorf tube: 50 mM BES, pH 7.0, 10 mM MgCl$_2$, 10 mM DTT, 0.1% TRITON X-100, 1 mM ApApC primer, 5 mM AppAp. The following procedures were performed:
cycle 1
(a) Add 2 ul (40 units) RNA Ligase (phage T4, New England Biolabs). Incubate at 37° C. for 2 hours. Heat at 95° C. for 5 minutes, cool to room temperature.
(b) Add 1 ul (3 units) Alkaline Phosphatase (calf intestine, US Biochemicals)+1 ul (2 units) Tobacco Acid Pyrophosphatase (Sigma). Incubate at 37° C. for 3.5 hours. Heat at 95° C. for 5 minutes, cool to room temperature.
cycle 2
(a) Add 10 ul 10 mM AppAp+1 ul RNA Ligase. Incubate at 37° C. for 30 minutes. Heat at 95° C. for 5 minutes, cool to room temperature.
(b) same as cycle 1
Insoluble coagulated protein debris was removed by pelleting at 12,000 g for 1 min. The only oligonucleotide product visible by USB TLC was the desired oligonucleotide product ApApCpApA. The final yield of oligonucleotide product was nearly 100%.

EXAMPLE 12

Synthesis of ApApC-pdApdA Using TdT+ddATP Capping

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppdAp. The following procedures were performed:
cycle 1
(a) Add 1 ul (20 units) RNA Ligase (phage T4, New England Biolabs). Incubate at 37° C. for 3 hours. Heat at 95° C. for 5 minutes, cool to room temperature.
(b) Add 1 ul Terminal deoxynucleotidyl Transferase (USB, 17 units/ul)+3 ul 5 mM dideoxyadenosine 5'-triphosphate. Incubate at 37° C. for 2.5 hours. Add 1 ug Proteinase K, incubate at 60° C. for 15 minutes, heat at 95° C. for 5 min, cool to room temperature.
(c) Add 1 ul (0.03 units) Nucleotide Pyrophosphatase (snake venom, Sigma P7383). Incubate at 37° C. for 30 minutes. Heat at 95° C. for 5 minutes, cool to room temperature.
(d) Add 1 ul (3 units) Alkaline Phosphatase (calf intestine, US Biochemicals). Incubate at 37° C. for 30 minutes. Heat at 95° C. for 5 minutes, cool to room temperature.
cycle 2
(a) Add 10 ul 10 mM AppdAp+1 ul RNA Ligase. Incubate at 37° C. for 15 hours. Heat at 95° C. for 5 minutes, cool to room temperature.
(b) same as cycle 1
(c) same as cycle 1
(d) same as cycle 1
Insoluble coagulated protein debris was removed by pelleting at 12,000 g for 5 min. The reaction mixture supernatant was analyzed by USB TLC. The only oligonucleotide product visible was the desired product ApApCpdApdA. The yield of final product was about 90% of the initial primer.

EXAMPLE 13

Synthesis of ApApC-DApA Using Enzyme-Solid Support Matrix

The following solution was placed in a total volume of 30 ul in an ependorf tube: 50 mM Tris-Cl, pH 8.0, 10 mM $MgCl_2$, 10 mM DTT, 0.1% TRITON X-100, 1 mM ApApC primer, 5 mM AppAp. The following procedures were performed:

cycle 1
(a) Add 1 ul (20 units) RNA Ligase (phage T4, New England Biolabs). Incubate at 37° C. for 1 hour. Heat at 95° C. for 5 minutes, cool to room temperature.
(b) Add 1 ul (0.03 units) Nucleotide Pyrophosphatase (snake venom, Sigma P7383). Incubate at 37° C. for 30 minutes. Heat at 95° C. for 5 minutes, cool to room temperature.
(c) Add 6 ul Alkaline Phosphatase-Acrylic Beads (calf intestine, Sigma Chemical Co.). Incubate at 37° C. for 2.5 hours with occasional mixing. Remove CIAP-acrylic beads by briefly pelleting. Heat supernatant at 95° C. for 5 minutes to remove any residual CIAP leakage, cool to room temperature.

cycle 2
(a) Add 10 ul 10 mM AppAp+1 ul RNA Ligase. Incubate at 37° C. for 2 hours. Heat at 95° C. for 5 minutes, cool to room temperature.
(b) same as cycle 1
(c) same as cycle 1, except skip the heat inactivation Insoluble coagulated protein debris was removed by pelleting at 12,000 g for 5 min. USB TLC revealed a mixture of approximately 50% ApApCpA and 50% ApApCpApA oligonucteotide product. The n–1 failure sequence was due to the incomplete 3'-dephosphorylation of the oligonucleotide in the first cycle. This example demonstrates that the enzymes can be covalently attached to a solid matrix.

EXAMPLE 14

The method of the invention can be used for synthesizing oligonucleotide mixtures in which two or more different bases are used at a particular position. This technique is known in the art as "wobbling" and is useful in hybridization applications of an oligonucleotide to a DNA library based on amino acid sequence. Wobbling is performed by adding a mixture of blocked nucleotide substrates instead of a single blocked nucleotide substrate during the RNA ligase step of one cycle. The relative amounts of the blocked nucleotides used is selected to balance out differences in coupling rate. For example, if a 50:50 mix of A and G is desired, a mixture of the nucleotide substrates AppAp and AppGp would be added during the RNA ligase step of the appropriate reaction cycle. If the reactivities of AppAp and AppGp are equal, the substrates would be used in equal amounts.

EXAMPLE 15

Synthesis of (ApApC)-pApA

The same protocol was used from example 3, except that after RNA Ligase coupling, the heat inactivation step in part (a) of each cycle was omitted, and 20 units additional RNA Ligase was added during each Alkaline Phosphatase digestion. USB TLC revealed pure ApApCpApA product with no visible n–1 or initial primer present. The yield of final product was about 90% of the initial primer.

This example demonstrates that inactivation of the chain extending enzyme is not necessary. In addition, the use of a thermostable chain extending enzyme would obviate the need to add this enzyme after each cycle. This example also demonstrates that phosphodiesterase I incubation can be performed without prior inactivation of the chain extending enzyme. Optionally, phosphodiesterase I incubation can be performed in the presence of 5'-Nucleotidase to hydrolyze AMF generated by phosphodiesterase I cleavage of App-(d)Np.

EXAMPLE 16

Synthesis of ApApCpApA with Substrate Reuse

The oligonucleotide ApApCpApA was synthesized according to the following procedure. The following solution was placed in a total volume of 30 ul in an ependorf tube: 50 mM Tris-Cl, pH 8.0, 10 mM $MgCl_2$, 10 mM DTT, 0.1% TRITON X-100, 1 mM ApApC initial primer, and Nucleotide Substrate. The following procedure was performed:

cycle 1
(a) Add 1 ul (20 units) T4 RNA Ligase (New England Biolabs), incubate at 37 degrees C. for 3 hours, heat at 85 degrees C. for minutes, cool.
(b) Add 1 ul (3 units) T4 Polynucleotide Kinase (US Biochemicals, contains 3'-Phosphatase), incubate at 37 degrees C. for 1 hour, heat at 85 degrees C for 5 minutes, cool.

cycle 2 - starting volume is 20 ul
(a) same as cycle 1. No AppAp substrate was added.
(b) same as cycle 1.

Sub-Example A: Nucleotide substrate was approximately 5 mM AppAp.

Sub-Example B: Nucleotide substrate was 5 mM 3',5'ADP+ 4.5 mM ATP. These precursors are converted to AppAp in the first cycle by RNA Ligase. Supplementation with inorganic pyrophosphatase in a separate experiment improved oligonucleotide product yield.

USB TLC confirmed the formation of ApApCpApA product for both sub-examples. USB TLC also confirmed that no significant inactivated nucleotide substrate AppA was formed for both sub-examples. Approximately 5 ul oligonucleotide product was incubated with 100 ng RNase A (US Biochemicals) at 37° C. for about 15 minutes. RNase A is used as a base-specific RNase to cleave the oligonucleotide 3' to the Cytidine base. Butyric TLC confirmed the formation of ApA oligonucleotide product for both sub-examples. Yield of oligonucleotide product was better in sub-example A.

This experiment demonstrates reuse in the Second cycle of nucleotide substrate AppAp used in the first cycle. This was accomplished by using bacteriophage T4 3'-Phosphatase under carefully controlled conditions to specifically remove the extended primer blocking group without significantly inactivating the nucleotide substrate AppAp. The high concentration of primer and nucleotide substrate used in this example and the following examples is for the convenience of allowing detection of product by thin layer chromatography. Proportionately lower concentrations, such as 0.10 mM primer and 1.0 mM nucleotide substrate may be more appropriate for long oligonucleotides to lessen the build up of side products.

EXAMPLE 17

Synthesis of ApApCpApA using Rye Grass 3'-Phosphatase

ApApCpApA was synthesized using the same procedure as Example 16, sub-example A, except 0.05 units 3'-Phosphatase from Rye Grass (Sigma, sold as 3'-Nucleotidase) was used for 3 hours at 37 degrees C. in place of T4 Polynucleotide Kinase (3'-Phosphatase). Butyric TLC confirmed synthesis of product and RNase A digestion confirmed formation of ApA.

EXAMPLE 18

Synthesis of ApApCpApA using Preferred Mode with Substrate Reuse

The following solution was placed in a total volume of 30 ul in an ependorf tube: 50 mM Tris-Cl, pH 8.0, 10 mM $MgCl_2$, 10 mM DTT, 0.1% Triton X-100, 1 mM ApApC initial primer, and 5 mM AppAp. The following procedure was performed:

cycle 1
(a) Add 1 ul (20 units) T4 RNA Ligase (New England Biolabs)+0.5 ul (0.025 units) 5'-Nucleotidase (Sigma), incubate at 37 degrees C. for 1 hour, heat at 85 degrees C. for 5 minutes, cool.
(b) Add Exonuclease—see details below. Heat at 95° C. for 5 minutes, cool.
(c) Add 0.5 ul (15 units) T4 Polynucleotide Kinase (US Biochemicals), incubate at 37 degrees C for 30 minutes, heat at 85 degrees C. for 5 minutes, cool.
cycle 2—starting volume is 20 ul
(a) same as cycle 1, but incubation is extended to 135 minutes. No AppAp substrate was added.
(b) same as cycle 1.
(c) same as cycle 1.
Sub-Example A: Exonuclease added was 1 ul (0.02 units) Phosphodiesterase I (US Biochemicals). In this sub-example only, 1 ul 100 mM ATP is added during RNA Ligase incubation in the second cycle to reform the substrate AppAp from 3',5'-ADP.
Sub-Example B: Exonuclease added was 1 ul (10 units) Exonuclease I (US Biochemicals)
Sub-Example C: Exonuclease added was 1 ul (0.1 units) Polynucleotide Phosphorylase (Sigma). In this sub-example only, 0.2 mM $Na_2AsO_4$ was incorporated in the buffer through-out the synthesis to facilitate Polynucleotide Phosphorylase digestion of unextended primer chains.
USB TLC confirmed the formation of ApApCpApA product in all sub-examples. Digestion with RNase A confirmed the formation of ApA in all sub-examples.

EXAMPLE 19

Synthesis of ApApCpApA using Substrate Reuse, and AMP Inactivating Enzyme(s)

The following solution was placed in a total volume of 30 ul in an ependorf tube: 50 mM Tris-Cl, pH 8.0, 10 mM $MgCl_2$, 10 mM DTT, 0.1% Triton X-100, 1 mM ApApC initial primer, and 5 mM AppAp. The following procedure was performed:
cycle 1
(a) Add 1 ul (20 units) T4 RNA Ligase (New England Biolabs)+AMP Inactivating Enzyme(s), incubate at 37° C. for 3 hours, heat at 85° C. for 5 minutes, cool.
(b) Add 1 ul (3 units) T4 Polynucleotide Kinase (US Biochemical), incubate at 37° C. for 1 hour, heat at 85° C. for 5 minutes, cool.
cycle 2
(a) same as cycle 1. No AppAp substrate is added.
(b) same as cycle 1.
Sub-Example A: AMP Inactivating Enzyme was 0.5 ul (0.025 units) 5'-Nucleotidase (Sigma)
Sub-Example B: AMP Inactivating Enzyme was 0.5 ul (0.025 units) 5'-Nucleotidase (Sigma)+1 ul (0.018 units) Adenosine Deaminase (Sigma).
Sub-Example C: AMP Inactivating Enzyme was 1 ul (0.004 units) AMP Deaminase (Sigma).
Sub-Example D: AMP Inactivating Enzyme was 1 ul (0.12 units) AMP Nucleosidase (E. coli).
USB TLC confirmed the formation of ApApCpApA product in all sub-examples. USB TLC also confirmed that the AMP Inactivating Enzymes in all sub-examples converted substantially all substrate to product. In all sub-examples, butyric TLC confirmed that the oligonucleotide ApA was cleaved from the product by RNase A digestion. It was also found that adenosine deaminase was not inactivated at 95° C., a useful property.

EXAMPLE 20

Synthesis of ApApCpApApdA using cycles with and without Substrate Reuse

The following solution was placed in a total volume of 30 ul in an ependorf tube: 50 mM Tris-Cl, pH 8.0, 10 mM $MgCl_2$, 10 mM DTT, 0.1% Triton X-100, 1 mM ApApC initial primer, and 5 mM AppAp. The following procedure was performed:
cycle 1: Reuse
(a) add 1 ul (20 units) T4 RNA Ligase (New England Biolabs), incubate at 37 degrees C. for 1 hour, heat at 85° C. for 5 minutes, cool.
(b) add 1 ul (3 units) T4 Polynucleotide Kinase (US Biochemicals), incubate at 37° C. for 1 hour, heat at 85° C. for 5 minutes, cool.
cycle 2: No Reuse
(a) add 1 ul (20 units) T4 RNA Ligase (New England Biolabs), incubate at 37 degrees C. for 1 hour, heat at 85° C. for 5 minutes, cool.
(b) add 1 ul (0.035 units) Nucleotide Pyrophosphatase (Sigma, snake venom), incubate at 37° C. for 30 minutes, heat at 95° C. for 5 minutes, cool.
(c) add 1 ul (1.6 units) Alkaline Phosphatase (US Biochemicals, calf intestine), incubate at 45° C. for 30 minutes, heat at 95° C. for 5 minutes, cool. (Alkaline Phosphatases generally have better activity at higher temperatures, such as 45°–60° C.).
cycle 3: No Reuse
(a) add 2 ul (40 units) T4 RNA Ligase (New England Biolabs)+10 ul 10 mM AppdAp, incubate at 37° C. for 80 minutes, heat at 85° C. for 5 minutes, cool.
(b) same as cycle: 2.
(c) same as cycle 2.
USB TLC strongly suggested formation of ApApCpApApdA product. Incubation of 5 ul oligonucleotide product with 100 ng RNase A (US Biochemicals) at 37° C. for 15 minutes resulted in the cleavage of the oligonucleotide to ApApdA product as strongly suggested by USB and buytric. Matrix assisted laser desorption mass spectroscopy confirms formation of this product.

I claim:

1. A method for synthesizing an oligonucleotide of a defined sequence, comprising the steps of:
   (a) combining (1) an oligonucleotide primer and (2) a blocked nucleotide or a blocked nucleotide precursor that forms a blocked nucleotide in situ, in a reaction mixture in the presence of a chain extending enzyme effective to couple the blocked nucleotide to the 3'-end of the oligonucleotide primer such that a primer-blocked nucleotide product is formed, wherein the blocked nucleotide comprises a nucleotide to be added to form part of the defined sequence and a blocking group attached to the 3'-end of the nucleotide effective to prevent the addition of more than one blocked nucleotide to the primer;
   (b) removing the blocking group from the 3'-end of the primer-blocked nucleotide product to form a primer-nucleotide product, whereby the reaction mixture contains any unreacted starting materials that may remain, primer-nucleotide product and reaction by-products; and
   (c) repeating at least one cycle of steps (a) and (b) using the primer-nucleotide product from step (b) as the oligonucleotide primer of step (a) in the subsequent cycle without separation of the primer-nucleotide product from the remainder of the reaction mixture.

2. A method according to claim 1, wherein the blocking group is removed enzymatically.

3. A method according to claim 2, wherein each cycle further comprises the additional step of inactivating unreacted blocked nucleotide in the reaction mixture to render it less reactive as a substrate for chain extending enzyme.

4. A method according to claim 3, wherein the chain extending enzyme is RNA ligase.

5. A method according to claim 4, wherein the blocked nucleotide is App(d)Np, where N represents any nucleoside or nucleoside analog which RNA ligase can couple to an oligonucleotide primer.

6. A method according to claim 5, wherein the blocking group is a phosphate and is removed from the primer-blocked nucleotide product by a phosphatase.

7. A method according to claim 5, wherein unreacted blocked nucleotide is inactivated by a phosphatase enzyme.

8. A method according to claim 5, wherein the unreacted blocked nucleotide is inactivated by a Dinucleotide Pyrophosphate Degrading Enzyme.

9. A method according to claim 1, wherein each cycle of steps further comprises the additional step of modifying uncoupled oligonucleotide primer to prevent its coupling to blocked nucleotide in subsequent cycles of the method.

10. A method according to claim 9, wherein the uncoupled oligonucleotide primer is modified by incubating with at least one Exonuclease, whereby the uncoupled oligonucleotide primer is degraded.

11. A method according to claim 9, wherein the uncoupled oligonucleotide primer is modified by incubating with a chain terminating nucleotide and an enzyme effective to couple the chain terminating nucleotide to uncoupled oligonucleotide primer, whereby uncoupled oligonucleotide primer is terminated.

12. A method according to claim 2, wherein the defined sequence includes at least one repeat region which is synthesized by a method comprising the steps of:
   (1) extending the oligonucleotide primer with 3'-phosphate-blocked nucleotide to form 3'-phosphate-blocked primer-nucleotide;
   (2) removing the 3'-phosphate blocking group from the 3'-phosphate-blocked primer-nucleotide substantially without removing the 3'-phosphate blocking group from unreacted 3'-phosphate-blocked nucleotide using 3'Phosphatase; and
   (3) repeating steps (1) and (2) using unreacted 3'-phosphate-blocked nucleotide from step (2) as the 3'-phosphate-blocked nucleotide of step (1).

13. A method for synthesizing a repeat region of an oligonucleotide having a defined sequence, said repeat region including a repeated nucleotide that appears more than once in succession, comprising the steps of:
   (a) enzymatically coupling an oligonucleotide primer with a 3'-phosphate-blocked repeated nucleotide to form a 3'-phosphate blocked primer-nucleotide;
   (b) removing the 3'-phosphate blocking group from the 3'-phosphate-blocked primer-nucleotide using 3'-phosphatase enzyme substantially without removing the 3'-phosphate blocking group from unreacted 3'-phosphate-blocked repeated nucleotide; and
   (c) repeating steps (a) and (b) using the unreacted 3'-phosphate-blocked repeated nucleotide from step (b) as the 3'-phosphate-blocked nucleotide of step (a) and using the deblocked primer-nucleotide product of step (b) as the oligonucleotide primer of step (a).

14. A method for synthesizing an oligonucleotide, wherein the 3'-end of an oligonucleotide primer is coupled with a blocked nucleotide to form a primer-blocked nucleotide product in a reaction mixture, said blocked nucleotide comprising a nucleotide to be added to the oligonucleotide primer and a blocking group attached to the 3'-end of the nucleotide effective to prevent the addition of more than one blocked nucleotide to the oligonucleotide primer, comprising incubating the reaction mixture with an exonuclease, whereby any oligonucleotide primer which was not coupled is degraded, substantially without degrading the primer-blocked nucleotide product.

15. A method for synthesizing an oligonucleotide, wherein the 3'-end of an oligonucleotide primer is enzymatically coupled with a blocked nucleotide to form a primer-blocked nucleotide product in a reaction mixture, said blocked nucleotide comprising a nucleotide to be added to the oligonucleotide primer and a removable blocking group attached to the 3'-end of the nucleotide effective to prevent the addition of more than one blocked nucleotide to the oligonucleotide primer, comprising incubating the reaction mixture with a chain terminating nucleotide and an enzyme effective to couple the chain terminating nucleotide to the oligonucleotide primer, whereby oligonucleotide primer which was not coupled to a blocked nucleotide is end-capped to render it unreactive to further coupling, said chain terminating nucleotide being different from said blocked nucleotide and selected such that end-capped oligonucleotide primer remains end-capped and unreactive when the blocking group is removed from the primer-blocked nucleotide product.

16. A method according to claim 15, wherein the chain terminating nucleotide is a dideoxynucleotide.

17. A method according to claim 14, wherein at least two nucleotides are added to the primer without intermediate purification of the resulting oligonucleotide product from other reactants and reaction by-products.

18. A method according to claim 1, wherein each cycle further comprises the additional step of converting adenosine monophosphate released in the coupling reaction to a less reactive form, whereby any inhibitory effect of the adenosine monophosphate pm the coupling of the oligonucleotide primer to the blocked nucleotide is minimized.

19. A method according to claim 1, further comprising the step of cleaving a synthesized oligonucleotide to remove some or all of the oligonucleotide primer used in the first cycle of the method from the synthesized oligonucleotide.

20. A method for coupling a blocked nucleotide AppNp to an oligonucleotide primer, characterized in that the blocked nucleotide is coupled to the primer using RNA Ligase in the absence of ATP, and in that pyrophosphate or unactivated nucleotide substrate, 3,5'-NDP, is used to regenerate free RNA Ligase from the inactivated adenylylated form, wherein N represents any nucleoside or nucleoside analog which RNA ligase can couple to an oligonucleotide primer.

21. A method for coupling a blocked nucleotide to an oligonucleotide primer, characterized in that the coupling is performed using RNA Ligase in the presence of 5'-Nucleotidase, AMP Nucleotidase or AMP Deaminase, whereby AMP released in the coupling reaction is converted to a form which is less effective than AMP to inhibit the coupling reaction or participate as a substrate in a reverse coupling reaction.

22. A method for synthesizing a selected oligonucleotide wherein an oligonucleotide primer is extended by enzymatically adding at least two nucleotides to the 3'-end of the oligonucleotide primer, characterized in that the primer is cleaved from the added nucleotides to form the selected oligonucleotide.

23. A method for converting a blocked nucleotide comprising a dinucleotide pyrophosphate moiety, a blocking group effective to prevent the enzymatic coupling of more than one blocked nucleotide to an oligonucleotide primer, and a nucleotide to be enzymatically coupled to the primer to a less reactive form, characterized in that the blocked nucleotide is treated with a dinucleotide pyrophosphate degrading enzyme.

24. A method according to claim 8, wherein the Dinucleotide Pyrophosphate Degrading Enzyme is Nucleotide Pyrophosphatase.

25. A method according to claim 23, wherein the Dinucleotide Pyrophosphate Degrading Enzyme is Nucleotide Pyrophosphatase.

26. A method according to claim 10, wherein the Exonuclease is exonuclease I, phosphodiesterase I, or polynucleotide kinase.

27. A method according to claim 14, wherein the Exonuclease is exonuclease L phosphodiesterase I, or polynucleotide kinase.

28. A method according to claim 18, wherein adenosine monophosphate is converted to a less reactive form using 5'-Nucleotidase.

29. A method according to claim 18, wherein adenosine monophosphate is converted to a less reactive form using AMP Nucleosidase.

* * * * *